(12) United States Patent
Zucherman et al.

(10) Patent No.: US 7,549,999 B2
(45) Date of Patent: Jun. 23, 2009

(54) INTERSPINOUS PROCESS DISTRACTION IMPLANT AND METHOD OF IMPLANTATION

(75) Inventors: James F. Zucherman, San Francisco, CA (US); Ken Y. Hsu, San Francisco, CA (US); Charles J. Winslow, Walnut Creek, CA (US); John Flynn, Concord, CA (US); Steve Mitchell, Pleasant Hill, CA (US); Scott Yerby, Montara, CA (US); Jay A. Markwart, Castro Valley, CA (US)

(73) Assignee: Kyphon SARL, Neuchatel (CH)

( * ) Notice: Subject to any disclaimer, the term of this patent is extended or adjusted under 35 U.S.C. 154(b) by 558 days.

(21) Appl. No.: 10/816,173

(22) Filed: Apr. 1, 2004

(65) Prior Publication Data
US 2005/0010298 A1  Jan. 13, 2005

Related U.S. Application Data

(60) Provisional application No. 60/472,817, filed on May 22, 2003.

(51) Int. Cl.
*A61F 5/00* (2006.01)
*A61F 2/30* (2006.01)
(52) U.S. Cl. .............. 606/249; 606/60; 606/53
(58) Field of Classification Search .......... 606/61, 606/60, 105, 249, 53; 623/17.11, 17.16
See application file for complete search history.

(56) References Cited

U.S. PATENT DOCUMENTS

| | | | |
|---|---|---|---|
| 2,456,806 A | 12/1948 | Wolffe | 33/174 |
| 2,677,369 A | 5/1954 | Knowles | 128/92 |
| 3,426,364 A | 2/1969 | Lumb | 3/1 |
| 3,643,658 A | 2/1972 | Steinemenan | 128/920 |
| 3,648,691 A | 3/1972 | Lumb | 128/920 |
| 3,867,728 A | 2/1975 | Stubstad | 3/1 |
| 3,875,595 A | 4/1975 | Froning | 3/1 |
| 4,034,418 A | 7/1977 | Jackson | 3/1.911 |
| 4,219,015 A | 8/1980 | Steinemenan | 128/92 D |
| 4,309,777 A | 1/1982 | Patil | 3/1.91 |
| 4,349,921 A | 9/1982 | Kuntz | 3/1 |

(Continued)

FOREIGN PATENT DOCUMENTS

| CA | 2015507 | 1/1991 |
|---|---|---|

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Pedro Philogene
(74) *Attorney, Agent, or Firm*—Coats & Bennett, P.L.L.C.

(57) ABSTRACT

An implant for positioning between the spinous processes, such as the spinous processes of cervical vertebrae, include first and second wings foe lateral positioning and a spacer located between the adjacent spinous processes. The implant can be positioned using minimally invasive procedures without modifying the bone or severing ligaments. The implant is shaped in accordance with the anatomy of the spine.

20 Claims, 16 Drawing Sheets

U.S. PATENT DOCUMENTS

| | | | |
|---|---|---|---|
| 4,369,769 A | 1/1983 | Edwards | 128/69 |
| 4,401,112 A | 8/1983 | Rezaian | 128/92 B |
| 4,455,690 A | 6/1984 | Homsy | 3/1 |
| 4,479,491 A | 10/1984 | Martin | 128/92 B |
| 4,501,269 A | 2/1985 | Bagby | 128/96 G |
| 4,553,273 A | 11/1985 | Wu | 623/18 |
| 4,554,914 A | 11/1985 | Kapp | 128/92 C |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,636,217 A | 1/1987 | Ogilvie | 623/17 |
| 4,643,178 A | 2/1987 | Nastari | 128/92 |
| 4,657,550 A | 4/1987 | Daher | 623/17 |
| 4,685,447 A | 8/1987 | Iversen | 128/1 R |
| 4,696,290 A | 9/1987 | Steffee | 128/69 |
| 4,714,469 A | 12/1987 | Kenna | 623/17 |
| 4,743,256 A | 5/1988 | Brantigan | 623/17 |
| 4,772,287 A | 9/1988 | Ray | 623/17 |
| 4,790,303 A | 12/1988 | Steffee | 128/924 M |
| 4,834,757 A | 5/1989 | Brantigan | 623/17 |
| 4,502,161 A | 7/1989 | Wall | 623/18 |
| 4,878,915 A | 11/1989 | Brantigan | 623/17 |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,923,471 A | 5/1990 | Morgan | 623/16 |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,888 A | 11/1990 | Scholten | 606/94 |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan et al. | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,180,381 A | 1/1993 | Aust | 606/61 |
| 5,192,327 A | 3/1993 | Brantigan | 623/17 |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,352,225 A | 10/1994 | Yuan | 606/61 |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,372 A | 3/1995 | Holt | 606/61 |
| 5,415,661 A | 5/1995 | Holmes | 606/69 |
| 5,437,672 A | 8/1995 | Alleyne | 606/61 |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A * | 3/1996 | Howland et al. | 606/249 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,736 A | 10/1996 | Ray | 623/17 |
| 5,571,191 A | 11/1996 | Fitz | 623/17 |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,658,286 A | 8/1997 | Sava | 606/61 |
| 5,672,177 A | 9/1997 | Seldin | 606/71 |
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,702,455 A | 12/1997 | Saggar | 623/17 |
| 5,725,582 A | 3/1998 | Bevan | 623/17 |
| 5,741,261 A | 4/1998 | Moskovitz | 606/79 |
| 5,766,251 A | 6/1998 | Koshino | 623/16 |
| 5,766,252 A | 6/1998 | Henry | 623/17 |
| 5,800,438 A | 9/1998 | Tuke | 606/90 |
| 5,824,098 A | 10/1998 | Stein | 623/20 |
| 5,836,948 A | 11/1998 | Zucherman | 606/61 |
| 5,860,977 A | 1/1999 | Zucherman | 606/61 |
| 5,865,846 A | 2/1999 | Bryan | 623/17 |
| 5,876,402 A | 3/1999 | Errico | 606/61 |
| 5,876,404 A | 3/1999 | Zucherman | 606/61 |
| 5,879,396 A | 3/1999 | Walston | 623/21 |
| 5,885,299 A | 3/1999 | Winslow | 606/99 |
| 5,888,224 A | 3/1999 | Beckers | 627/17 |
| 5,888,226 A | 3/1999 | Rogozinski | 623/17 |
| 5,951,555 A | 9/1999 | Rehak | 606/61 |
| 5,976,186 A | 11/1999 | Bao | 623/17 |
| 6,001,130 A | 12/1999 | Bryan | 623/17 |
| 6,022,376 A | 2/2000 | Assell | 623/17 |
| 6,030,162 A | 2/2000 | Huebner | 411/413 |
| 6,045,552 A | 4/2000 | Zucherman | 606/61 |
| 6,045,554 A | 4/2000 | Grooms | 606/73 |
| 6,048,204 A | 4/2000 | Klardie | 433/174 |
| 6,048,342 A | 4/2000 | Zucherman | 606/61 |
| 6,048,344 A | 4/2000 | Schenk | 606/73 |
| 6,068,630 A | 5/2000 | Zucherman | 606/61 |
| RE36,758 E | 6/2000 | Fitz | 623/17 |
| 6,074,390 A | 6/2000 | Zucherman | 606/61 |
| 6,090,112 A * | 7/2000 | Zucherman et al. | 606/249 |
| 6,099,531 A | 8/2000 | Bonutti | 606/87 |
| 6,113,639 A | 9/2000 | Ray | 623/17.16 |

| | | | | | | |
|---|---|---|---|---|---|---|
| 6,129,730 A | 10/2000 | Bono ................ 606/73 | | 6,712,852 B1 | 3/2004 | Chung ............ 623/17.11 |
| 6,132,464 A | 10/2000 | Martin ............. 623/17 | | 6,730,127 B2 | 5/2004 | Michelson ........ 623/17.16 |
| 6,139,550 A | 10/2000 | Michelson ............ 606/69 | | 6,746,484 B1 | 6/2004 | Liu et al. |
| 6,149,652 A | 11/2000 | Zucherman ............ 606/61 | | 6,746,485 B1 | 6/2004 | Zucherman ........ 623/17.16 |
| 6,152,926 A | 11/2000 | Zucherman ............ 606/61 | | 6,752,831 B2 | 6/2004 | Sybert ............ 623/13.17 |
| 6,152,927 A | 11/2000 | Farris ................ 606/69 | | 6,755,841 B2 | 6/2004 | Fraser ................ 606/99 |
| 6,156,038 A | 12/2000 | Zucherman ............ 606/61 | | 6,761,720 B1 | 7/2004 | Senegas ............ 606/61 |
| 6,156,067 A | 12/2000 | Bryan ............ 623/17.15 | | 6,764,491 B2 | 7/2004 | Frey et al. |
| 6,183,471 B1 | 2/2001 | Zucherman ............ 606/61 | | 6,783,527 B2 | 8/2004 | Drewry ................ 606/61 |
| 6,190,387 B1* | 2/2001 | Zucherman et al. .......... 606/61 | | 6,796,983 B1 | 9/2004 | Zucherman ............ 606/61 |
| 6,190,414 B1 | 2/2001 | Young ............ 623/17.15 | | 6,800,670 B2 | 10/2004 | Shen ................ 522/153 |
| 6,193,721 B1 | 2/2001 | Michelson ............ 606/70 | | 6,811,567 B2 | 11/2004 | Reiley ............ 623/17.11 |
| 6,200,322 B1 | 3/2001 | Branch ................ 606/96 | | 6,902,566 B2 | 6/2005 | Zucherman ............ 606/61 |
| 6,206,922 B1 | 3/2001 | Zdeblick ............ 623/17.11 | | 6,926,728 B2 | 8/2005 | Zucherman et al. ........ 606/190 |
| 6,217,580 B1 | 4/2001 | Levin ................ 606/71 | | 2001/0012938 A1 | 8/2001 | Zucherman |
| 6,224,599 B1* | 5/2001 | Baynham et al. ............ 606/61 | | 2001/0018614 A1 | 8/2001 | Bianchi |
| 6,224,602 B1 | 5/2001 | Hayes ................ 606/69 | | 2002/0004683 A1 | 1/2002 | Michelson |
| 6,224,607 B1 | 5/2001 | Michelson ............ 606/96 | | 2002/0016595 A1 | 2/2002 | Michelson |
| 6,228,900 B1 | 5/2001 | Shen ................ 522/153 | | 2002/0022843 A1 | 2/2002 | Michelson |
| 6,234,705 B1 | 5/2001 | Troxell ............ 403/237 | | 2002/0065557 A1 | 5/2002 | Goble |
| 6,235,030 B1 | 5/2001 | Zucherman ............ 606/61 | | 2002/0072800 A1 | 6/2002 | Goble |
| 6,238,397 B1 | 5/2001 | Zucherman ............ 606/61 | | 2002/0077700 A1 | 6/2002 | Varga |
| 6,261,296 B1 | 7/2001 | Aebi ................ 606/90 | | 2002/0099376 A1 | 7/2002 | Michelson |
| 6,280,444 B1 | 8/2001 | Zucherman ............ 606/61 | | 2002/0128655 A1 | 9/2002 | Michelson |
| 6,293,949 B1 | 9/2001 | Justis ................ 606/61 | | 2002/0133155 A1 | 9/2002 | Ferree |
| 6,299,642 B1* | 10/2001 | Chan ............ 623/16.11 | | 2002/0151895 A1 | 10/2002 | Soboleski |
| 6,306,136 B1 | 10/2001 | Baccelli ............ 606/61 | | 2002/0183756 A1 | 12/2002 | Michelson |
| 6,332,882 B1 | 12/2001 | Zucherman ............ 606/61 | | 2002/0183757 A1 | 12/2002 | Michelson |
| 6,332,883 B1 | 12/2001 | Zucherman ............ 606/61 | | 2002/0188296 A1 | 12/2002 | Michelson |
| 6,352,537 B1 | 3/2002 | Strnad ................ 606/61 | | 2003/0004572 A1 | 1/2003 | Goble |
| 6,368,351 B1 | 4/2002 | Glenn ............ 623/17.15 | | 2003/0028250 A1 | 2/2003 | Reiley |
| 6,371,984 B1 | 4/2002 | Van Dyke ........ 623/11.11 | | 2003/0040746 A1 | 2/2003 | Mitchell |
| 6,379,355 B1 | 4/2002 | Zucherman ............ 606/61 | | 2003/0060828 A1 | 3/2003 | Michelson |
| 6,383,186 B1 | 5/2002 | Michelson ............ 606/69 | | 2003/0078668 A1 | 4/2003 | Michelson |
| 6,383,191 B1* | 5/2002 | Zdeblick et al. ............ 606/105 | | 2003/0181912 A1 | 9/2003 | Michelson |
| 6,395,030 B1 | 5/2002 | Songer ............ 623/17.11 | | 2003/0191471 A1 | 10/2003 | Michelson |
| 6,398,783 B1 | 6/2002 | Michelson ............ 606/69 | | 2003/0191472 A1 | 10/2003 | Michelson |
| 6,402,756 B1 | 6/2002 | Ralph ................ 606/71 | | 2003/0191532 A1 | 10/2003 | Goble |
| 6,416,776 B1 | 7/2002 | Shamie ............ 424/423 | | 2003/0204259 A1 | 10/2003 | Goble |
| 6,419,676 B1 | 7/2002 | Zucherman ............ 606/61 | | 2004/0006391 A1 | 1/2004 | Reiley |
| 6,419,677 B2 | 7/2002 | Zucherman ............ 606/61 | | 2004/0049272 A1 | 3/2004 | Reiley |
| 6,419,703 B1 | 7/2002 | Fallin ............ 623/17.11 | | 2004/0049273 A1 | 3/2004 | Reiley |
| 6,428,542 B1 | 8/2002 | Michelson ............ 606/70 | | 2004/0049274 A1 | 3/2004 | Reiley |
| 6,436,145 B1 | 8/2002 | Miller ............ 623/20.34 | | 2004/0049275 A1 | 3/2004 | Reiley |
| 6,440,169 B1 | 8/2002 | Elberg et al. ........ 623/17.16 | | 2004/0049276 A1 | 3/2004 | Reiley |
| 6,451,019 B1 | 9/2002 | Zucherman ............ 606/61 | | 2004/0049277 A1 | 3/2004 | Reiley |
| 6,451,020 B1 | 9/2002 | Zucherman ............ 606/61 | | 2004/0049278 A1 | 3/2004 | Reiley |
| 6,454,771 B1 | 9/2002 | Michelson ............ 606/70 | | 2004/0049281 A1 | 3/2004 | Reiley |
| 6,458,131 B1 | 10/2002 | Ray ................ 606/61 | | 2004/0087948 A1 | 5/2004 | Suddaby |
| 6,478,796 B2 | 11/2002 | Zucherman ............ 606/61 | | 2004/0111154 A1 | 6/2004 | Reiley |
| 6,500,178 B2 | 12/2002 | Zucherman ............ 606/61 | | 2004/0116927 A1 | 6/2004 | Graf |
| 6,514,256 B2 | 2/2003 | Zucherman ............ 606/61 | | 2004/0122427 A1 | 6/2004 | Holmes |
| 6,527,776 B1 | 3/2003 | Michelson ............ 606/70 | | 2004/0127989 A1 | 7/2004 | Dooris |
| 6,558,423 B1 | 5/2003 | Michelson ........ 623/17.11 | | 2004/0143268 A1 | 7/2004 | Falahee |
| 6,558,686 B1 | 5/2003 | Darouiche ............ 424/423 | | 2004/0181226 A1 | 9/2004 | Michelson |
| 6,565,570 B2 | 5/2003 | Sterett ................ 606/69 | | 2004/0181229 A1 | 9/2004 | Michelson |
| 6,565,605 B2 | 5/2003 | Goble ............ 623/17.11 | | 2004/0186475 A1 | 9/2004 | Falahee |
| 6,579,318 B2 | 6/2003 | Varga ............ 623/17.11 | | 2004/0186476 A1 | 9/2004 | Michelson |
| 6,579,319 B2 | 6/2003 | Goble ............ 623/17.11 | | 2004/0210313 A1 | 10/2004 | Michelson |
| 6,582,433 B2 | 6/2003 | Yun ................ 606/61 | | 2004/0210314 A1 | 10/2004 | Michelson |
| 6,582,437 B2 | 6/2003 | Dorchak ............ 606/90 | | 2004/0220678 A1 | 11/2004 | Chow |
| 6,592,586 B1 | 7/2003 | Michelson ............ 606/71 | | 2004/0230201 A1 | 11/2004 | Yuan |
| 6,610,091 B1 | 8/2003 | Reiley ............ 623/17.11 | | 2004/0230304 A1 | 11/2004 | Yuan |
| 6,620,163 B1 | 9/2003 | Michelson ............ 606/61 | | 2004/0236334 A1 | 11/2004 | Michelson |
| 6,626,944 B1 | 9/2003 | Taylor ............ 623/17.16 | | 2004/0236335 A1 | 11/2004 | Michelson |
| 6,641,585 B2 | 11/2003 | Sato et al. ............ 606/61 | | 2005/0027297 A1 | 2/2005 | Michelson |
| 6,652,527 B2 | 11/2003 | Zucherman ............ 606/61 | | 2005/0027298 A1 | 2/2005 | Michelson |
| 6,652,534 B2 | 11/2003 | Zucherman ............ 606/102 | | | | |
| 6,669,729 B2 | 12/2003 | Chin ............ 623/17.11 | | | | |
| 6,695,842 B2 | 2/2004 | Zucherman ............ 606/61 | | FOREIGN PATENT DOCUMENTS | | |
| 6,699,246 B2 | 3/2004 | Zucherman ............ 606/61 | | DE | 2821678 A1 | 4/1980 |
| 6,699,247 B2 | 3/2004 | Zucherman ............ 606/61 | | DE | 3113142 A1 | 1/1982 |
| 6,712,819 B2 | 3/2004 | Zucherman ............ 606/61 | | DE | 4012622 C1 | 7/1991 |

| | | |
|---|---|---|
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| JP | 10-179622 | 7/1998 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 02/34120 A2 | 5/2002 |
| WO | WO 02/051326 | 7/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

\* cited by examiner

INTERSPINOUS PROCESS DISTRACTION IMPLANT AND METHOD OF IMPLANTATION

CLAIM OF PRIORITY

This application claims priority to U.S. Provisional Application No. 60/472,817, filed May 22, 2003, entitled "Cervical Interspinous Process Distraction Implant and Method of Implantation".

FIELD OF THE INVENTION

This invention relates to a cervical interspinous process implant.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the cervical spine. Such implants would distract, or increase the space between, the vertebrae to increase the foraminal area and reduce pressure on the nerves and blood vessels of the cervical spine.

A further need exists for development of a minimally invasive surgical implantation method for cervical spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

BRIEF DESCRIPTION OF THE DRAWINGS

FIG. 1 provides a perspective view of an embodiment of an implant of the present invention having a spacer, a distraction guide, and a wing with a cross-sectional elliptical shape. The spacer has a teardrop shape in cross-section perpendicular to its longitudinal axis. FIG. 2 is an end view of the embodiment of the invention in FIG. 1.

FIG. 3 is a perspective view of another embodiment of the invention having a wing that is teardrop-shaped in cross-section substantially perpendicular to the longitudinal axis of the spacer. FIG. 4 is an end view of a second wing for the embodiment of the invention of FIG. 3.

FIG. 5 is a perspective view of an embodiment of the invention having a rotatable spacer and a wing that is elliptical in cross-section. FIG. 6 is a perspective view of an embodiment of the invention having a rotatable spacer with two wings that are teardrop-shaped in cross-section. The second wing becomes connected with the spacer after the distraction guide, spacer, and wing are positioned in the cervical spine during surgery. FIG. 7 depicts the axis of rotation as seen from an end view of the embodiment of the invention of FIG. 6.

FIG. 8 is a perspective view of an embodiment of the invention with a wing that is truncated at its posterior end. FIG. 9A is an end view of an embodiment of the invention with a wing truncated at its posterior end, with a rotatable spacer. FIG. 9B is a truncated second wing for the two-winged version of the embodiment of the invention of FIG. 9A.

FIG. 10 is a plan view of an embodiment of the invention where a screw is used to secure a second wing to the spacer. FIG. 11 shows a perspective view of the second wing of this embodiment of the invention. FIG. 12 shows a perspective view of this embodiment of the invention.

FIG. 13A is a side view of an embodiment of a second wing of the invention, depicting a flexible hinge mechanism for securing the second wing to the implant during surgery. FIG. 13B is a side-sectional view of the second wing of FIG. 13A through line 13B-13B. FIG. 14A is a plan view of the first wing, spacer, and distraction guide depicting the indentation in the spacer that fits with the hinge of the second wing of the embodiment of FIGS. 13A and 13B. FIG. 14B is a front view of the second wing with flexible hinge of the embodiment of FIGS. 13A and 13B.

FIG. 15A is a top view of the an embodiment of the invention of FIG. 3, positioned between the spinous processes of adjacent cervical vertebrae, which embodiment has wings with anterior ends directed away from the center of the spacer, and truncated posterior ends. FIG. 15B is a top view of the implant of FIG. 15A. FIG. 16 is a top view of two such implants of the invention as seen in FIG. 15, positioned in the cervical spine.

DETAILED DESCRIPTION OF THE PREFERRED EMBODIMENTS OF THE INVENTION

Figure 1:
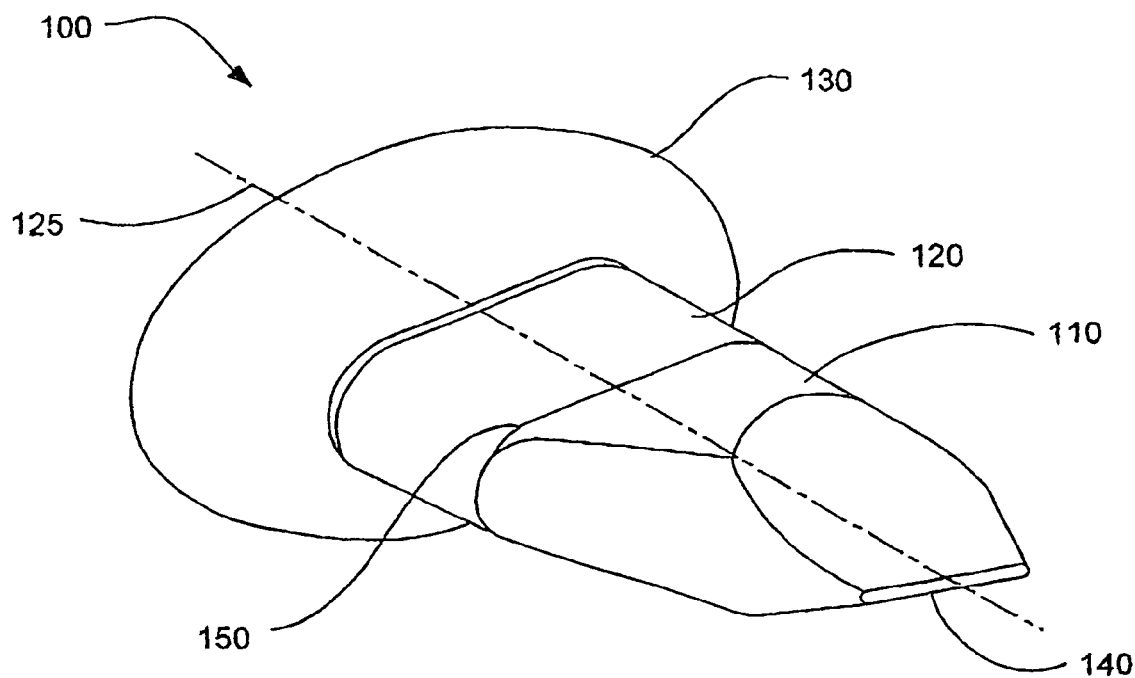
FIGS. 1 and 2.

The embodiment of the invention includes a cervical spine implant for alleviating discomfort associated with the cervical spine without damage to the bones or other anatomical structures associated with the spine. The embodiment also encompasses a method for minimally invasive surgical implantation.

An embodiment of cervical spine implant of the invention taught herein is adapted specifically to accommodate the anatomy of the cervical spine and to distract the vertebrae to increase the foraminal area and relieve pressure on the nerve roots. This embodiment of the implant is shaped with smooth, broad sides so that, when it is positioned during surgical implantation between the spinous processes of adjacent cervical vertebrae, the implant distributes the forces acting on it from the bones of the cervical spine. Thus positioned, the implant distracts the cervical spine to alleviate the pressure and restrictions on blood vessels and nerves affected by stenosis and other spinal conditions.

The embodiment of the invention further discloses a method for minimally invasive surgical implantation. The method for implantation taught herein accommodates structures associated with the cervical spine, and minimizes the need for invasive surgery. As only one example, it is of obvious importance to avoid surgical injury to the *ligamentum nuchae* (supraspinous ligament) in the dorsal neck, a structure which cushions the spinous processes of the upper cervical vertebrae.

While the cervical spine implant and method for relieving pain address the needs of the elderly for relief of symptoms of stenosis and the like, the embodiment of the invention also can be used with individuals of all ages and sizes where distraction of the spinous processes would be beneficial.

The implant is characterized in one embodiment as including a distraction guide, a spacer, and a wing. The distraction guide extends from one end of the spacer and is shaped so that it can distract the spinous processes of adjacent cervical vertebrae so that the spacer then can be urged into place between the spinous processes. A single lateral retaining unit called a wing prevents lateral displacement and rejection of the implant. The wing either extends from or is attached to the spacer.

In another embodiment of the invention, the implant includes a first unit having a spacer with a distraction guide and a first wing. The embodiment further includes a second wing which fits over the distraction guide to connect with the spacer, and a means for securing the second wing to the spacer. The two wings prevent lateral displacement and rejection of the implant.

In a further embodiment of the present invention, the implant includes a spacer that is rotatable relative to the wing of the implant. The spacer, which is tear-dropped shaped in cross-section, is received over the shaft of the implant and can rotate thereon about the shaft. It is to be understood that the spacer need not be teardrop-shaped in cross-section; rather, other forms are possible, including but not limited to cylindrical, ovoid, elliptical, and the like.

It is to be understood that the cortical bone of the spinous processes is stronger at an anterior position, near the vertebral bodies of the vertebra, than at a posterior position distally located from the vertebral bodies. The advantage to using a rotatable spacer is that the rotation allows the surgeon more easily to position the implant anteriorly between spinous processes of adjacent cervical vertebrae.

An additional feature of the implant is its flat surfaces for load bearing. The flat surfaces in contact with the bone distribute the forces that bear on the bones and the implant because of the distraction.

As maybe required for securing the lateral position of the implant between the spinous processes, a second wing can be connected with the spacer on the end of the spacer that joins with the distraction guide. To connect the second wing, the second wing passes over the distraction guide and is received by the spacer. A fastener is used to secure the second wing to the spacer.

In yet another embodiment of the implant, the wing or wings have truncated posterior ends to avoid or minimize interaction of the implants and interference with neck rotation. For example, an implant with extended posterior wings, positioned between cervical vertebrae five and six, and a similar implant, placed between cervical vertebrae six and seven, might interfere with each other at the posterior ends of the wings during cervical rotation, depending on the dimensions of a particular patient's vertebrae and surrounding structures. Truncating the posterior ends of the wings can avoid the undesirable consequences of two implants' interaction.

In a further embodiment of the present invention, the anterior portions of the first and second wings flare outward at an angle from the spacer and away from the anterior ends of each other, in order to accommodate the wedge shape of spinous processes of the certain cervical vertebrae of the cervical spine.

In another embodiment, stops or keeps are placed around the posterior ends of the spinous processes of adjacent cervical vertebrae between which the implant of any of the above described embodiments is positioned. The keeps prevent backward displacement of the implant. The keeps can be made of a biocompatible, flexible polymer. Addifionally, the keeps can be made of stainless steel, titanium, or a shape memory material such as Nitinol.

It is to be understood that the distraction guide, spacer, and wings can be of various shapes. For example, the distraction guide can be wedge-shaped or any other shape that introduces distraction between spinous processes of adjacent cervical vertebrae. The spacers, too, can have alternative shapes, defined by their cross sections as teardrop, elliptical, ovoid, etc., which would provide smooth edges and a flat and smooth contact surface area between the spinous processes and the spacer to distribute the forces placed thereon by the bone. The wings also might be teardrop-shaped, elliptical, ovoid, etc., in cross-section, or any other shape that provides smooth flat surfaces and rounded edges.

In yet another aspect of the invention, a method is presented for relieving pain due to the development of, by way of example only, stenosis and facet arthropathy of the cervical spine. The method is comprised of the steps of accessing the spinous processes of adjacent cervical vertebrae and implanting a cervical spinal distraction device in order to achieve the desired distraction and to maintain that distraction.

One aspect of the method taught is the use of a guide wire through the neck to guide the positioning of the implant while monitoring the implantation via x-ray.

Other aspects, objects, features and elements of embodiments of the invention are described or evident from the accompanying specification, claims and figures.

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 2:
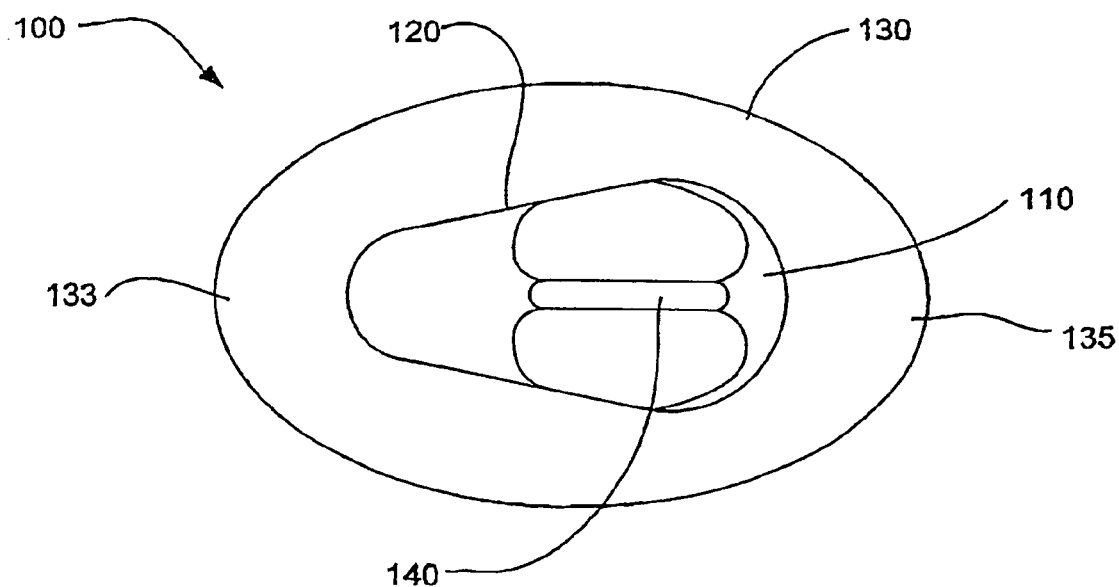

An embodiment of an implant 100 of the invention is depicted in FIGS. 1 and 2. This implant 100 includes a wing 130, a spacer 120, and a lead-in tissue expander, or a distraction guide 110. The distraction guide 110 in this particular embodiment is wedge-shaped, i.e., has an expanding cross-section from the end distal 140 to the region 150 where the guide 110 joins with the spacer 120. As such, the distraction guide functions to initiate distraction of the soft tissue and the spinous processes when the implant 100 is surgically inserted between the spinous processes. It is to be understood that the distraction guide can be pointed and the like, in order to facilitate insertion of the implant between the spinous processes of adjacent cervical vertebrae. It is advantageous that the insertion technique disturb as little of the bone and surrounding tissue or ligaments as possible in order to (1) reduce trauma to the site and promote early healing; and (2) prevent destabilization of the normal anatomy. It is to be noted that with the present embodiment, and all of the embodiments herein, there is no requirement to remove any of the bone of the spinous processes and no requirement to remove or sever ligaments and tissues immediately associated with the spinous processes. Specifically, it is unnecessary to remove or sever the ligamentum nuchae, (supraspinous ligament) which partially cushions the spinous processes of the upper cervical vertebrae.

Figure 3:
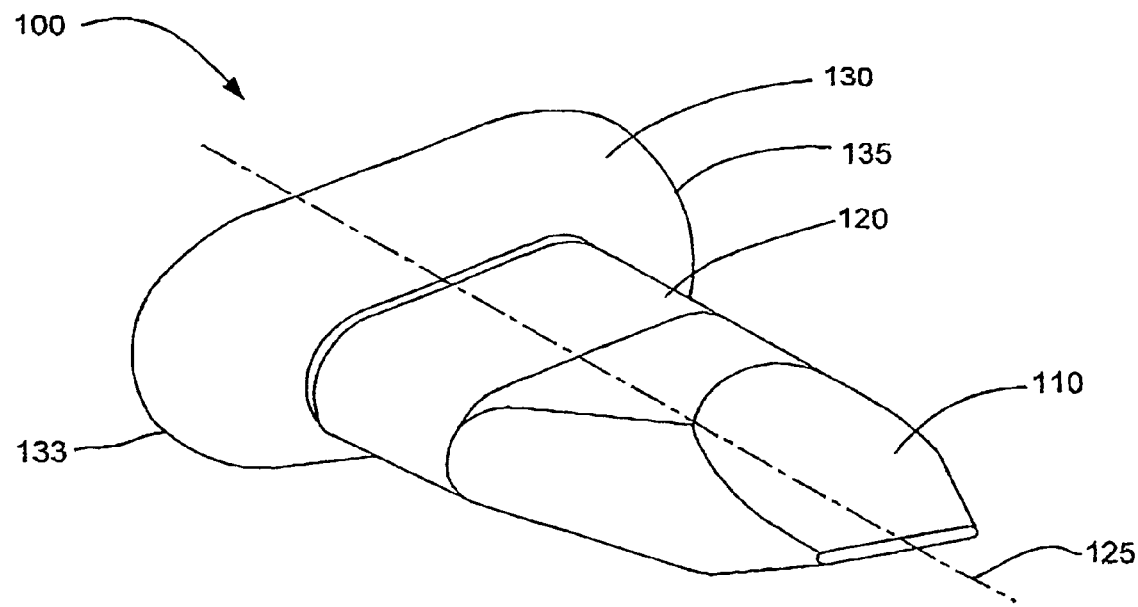
FIGS. 3 and 4.

Additionally, as depicted in FIGS. 1 and 2, the wing 130 in this embodiment 100 is elliptically-shaped in a cross-section perpendicular to the longitudinal axis 125 of the spacer and distraction guide. As illustrated in the embodiment of FIG. 3, and as discussed in more detail herein, the wing 130 can have alternative shapes in cross-section, such as teardrop, wedge, circular, oval, ovoid, football-shaped, and rectangular-shaped with rounded corners and other shapes, and be within the spirit and scope of the invention. The wing 130 has an anterior portion 133 and a posterior portion 135.

Further, as also can be seen in FIGS. 1, 2, and 3 and other embodiments to be discussed herein, the spacer 120 is teardrop-shaped in cross-section perpendicular to the spacer's longitudinal axis 125. The spacer 120, like the wing 130, can have alternative shapes such as circular, wedge, oval, ovoid, football-shaped, and rectangular-shaped with rounded corners and other shapes, and be within the spirit and scope of the invention. The shape of the spacer selected for a particular patient should accommodate the wedge-like space between adjacent cervical spinous processes and thus allow the surgeon to position the implant as close as possible anteriorly, near the vertebral bodies.

It should be appreciated that the shape selected for the spacer 120 should create a smooth, flat and relatively broad contact area between the implant 100 and the spinous processes of the vertebrae that are to be subject to distraction. Increasing the contact surface area between the implant and the spinous processes distributes the force and load between the spinous frame and the implant. Generally, a teardrop or wedge-shaped spacer allows for more load-bearing contact between the spacer and the spinous process.

Figure 4:
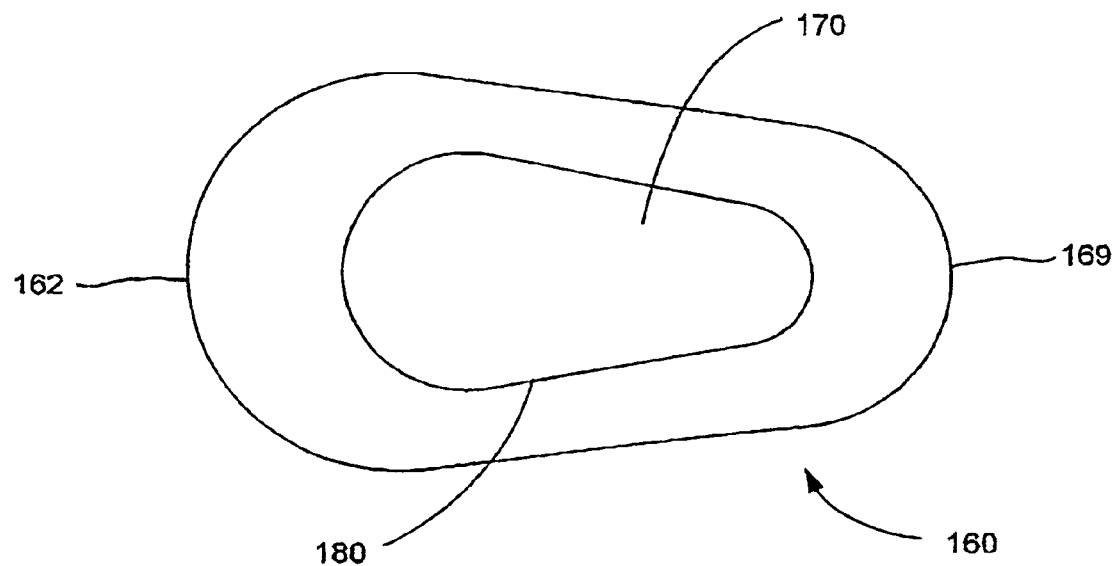

It is to be understood also that the implant 100 can have two wings, with a second wing 160 (FIG. 4) separate from the distraction guide 110, spacer 120 and first wing 130. The second wing can be connected to the end of the spacer 120 distal from the first wing 130. It should be noted that the second wing 160, like the first wing 130, can prevent lateral displacement of the implant 100 relative to an individual patient's cervical spine anatomy. In FIG. 4, the second wing 160 is teardrop-shaped and wedge-shaped in cross-section. The wider section or end 162 of the teardrop shape is the posterior end of the second wing 160 and the narrower section or end 169 is the anterior end of the second wing 160. Unlike the first wing 130, however, the sides of the second wing 60 define a space 170 with a lip 180 that allows the second wing 160 to pass over ditraction guide 110 to meet and connect with the spacer 120. The second wing 160 is then secured to the spacer 120 toward the end of the spacer located distally from the first wing 140. The second wing 60 is implanted once the distraction guide 110, spacer 120, and first wing 130 are inserted as a unit between the spinous processes of adjacent cervical vertebrae.

It is to be understood that the implant is preferably made in two pieces. The first piece includes the first wing 130, the spacer 120, and the distraction guide 110. The second piece includes the second wing 160. Each piece can be made in a number of ways known in the art including by machining and molding. Each piece, as will be more fully discussed can be made of any material that is bio-compatible with the body of a patient. For example the implants can be made of stainless steel and titanium. Additionally, a shape memory metal such as Nitinol, which is a combination of titanium and nickel, can also be used. Further polymers such as described later can also be used. It is further to be understood that the implant can be formed with multiple pieces and with the pieces appropriately joined together. Further the implant can be formed as one piece or joined together as one piece and be within the spirit and scope of the invention, but without some of the advantages of the embodiment of the invention as exist with a two piece embodiment as shown in FIGS. 1, 2, 3, and 4.

Figure 5:
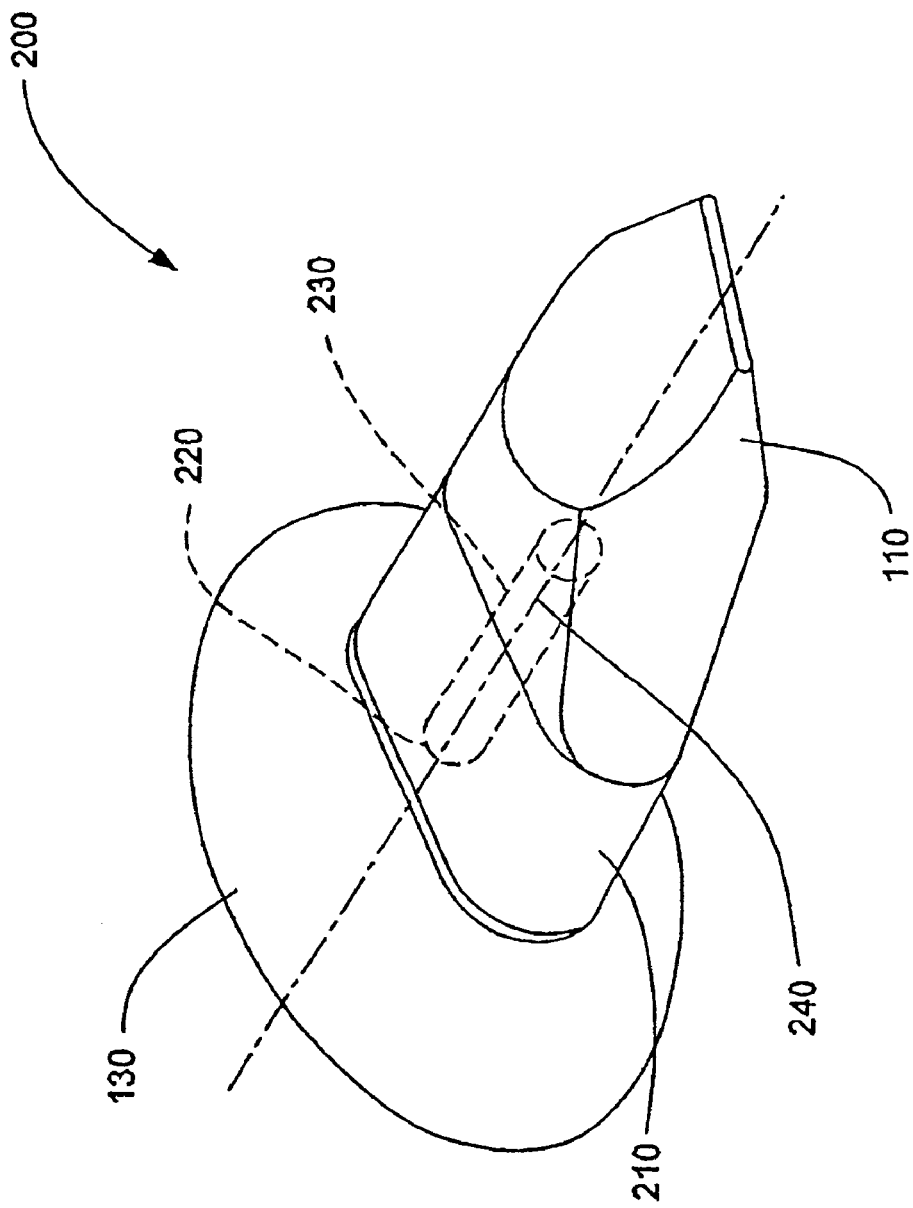
FIGS. 5, 6, and 7.
Figure 6:
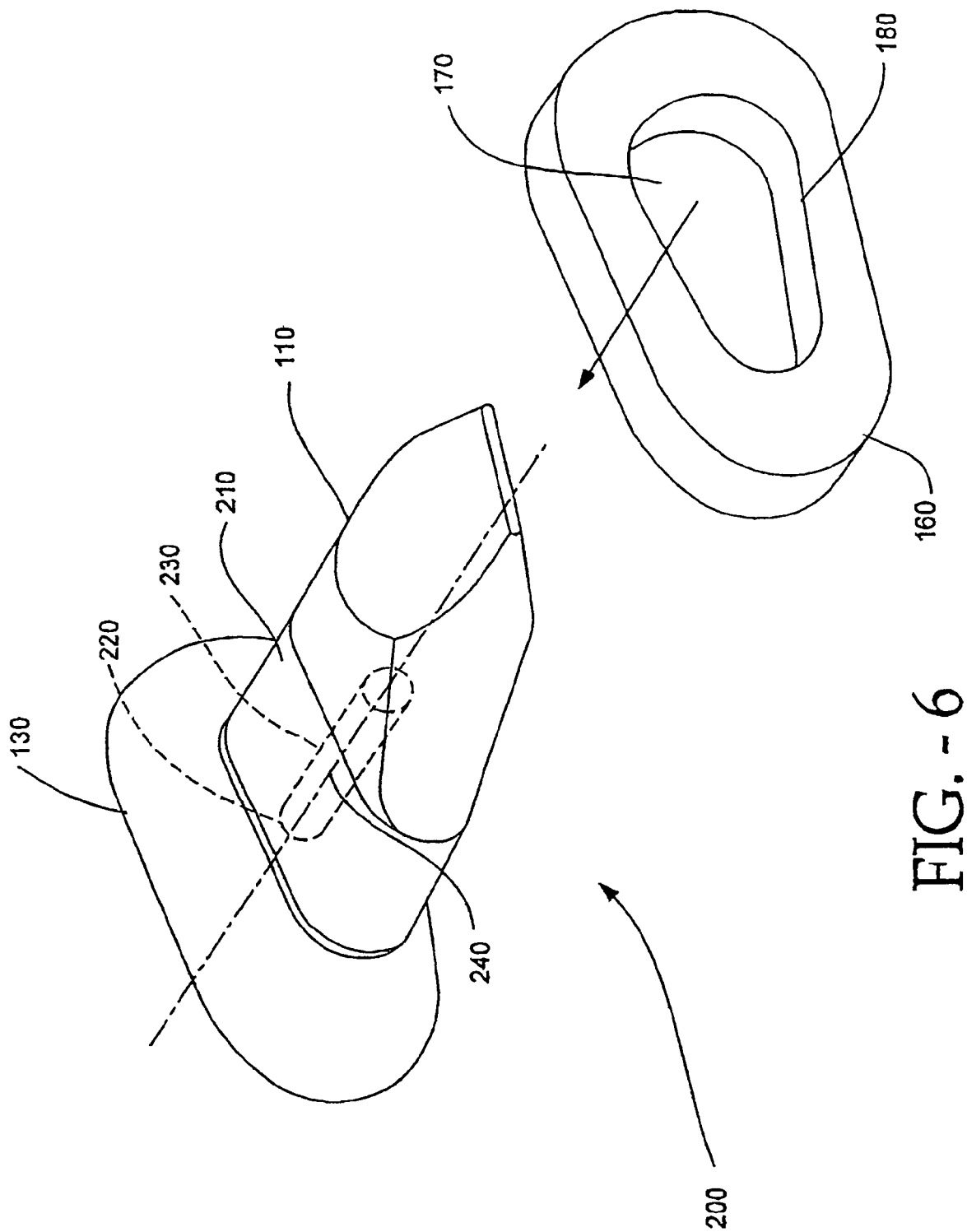
Figure 7:
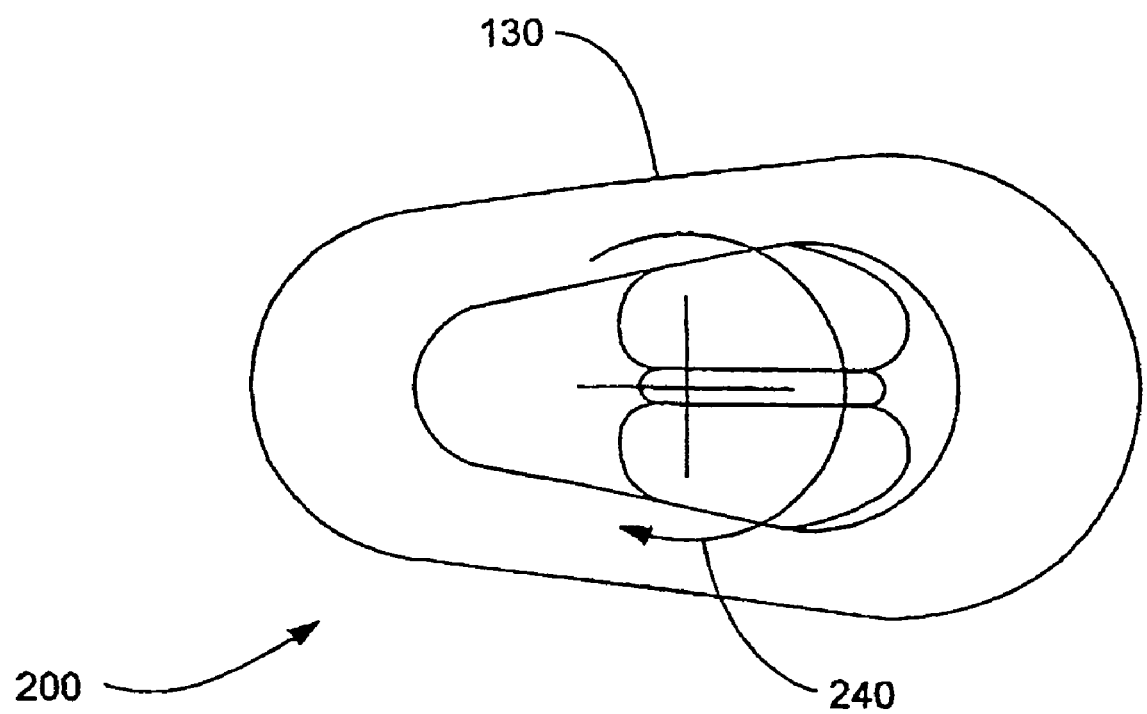

A further embodiment 200 of the invention is depicted in FIGS. 5 and 6. In this embodiment 200, the spacer 210 is rotatable about its longitudinal axis 240, FIG. 7 relative to a first wing 130 (FIG. 5), or relative to two wings with respect to an alternative embodiment of the invention (FIG. 6). The spacer may also be rotatable or fixed, relative to the distraction guide 110. The spacer 210 has a bore 220 running the length of its longitudinal axis 240, with holes at both ends of the spacer 210, and a shaft 230inserted through the bore 220 and connecting with the distraction guide 110 and first wing 130. As discussed above, it maybe advantageous to position any of the implants taught herein as close as possible to the vertebral bodies. The rotatable spacer 210 can accommodate the bone structures of the cervical spine as the implant is inserted between the spinous processes as it follows the distraction guide laterally into position. Spacer rotation accommodates the anatomy of the spinous processes relative to the wings of the implant. Thus, the rotatable spacer 210 improves the positioning of the spacer independent of the wings relative to the spinous processes. The embodiment of FIG. 6 has a first wing 130 and if desired, a second wing 160 similar to the wing depicted in the embodiment of FIG. 3. As will be discussed below, the shape of the wings in FIGS. 3 and 6 is such that the implants accommodate the twisting of the cervical spine along its axis as, for example, the head of a patient turning from side to side.

Figure 8:
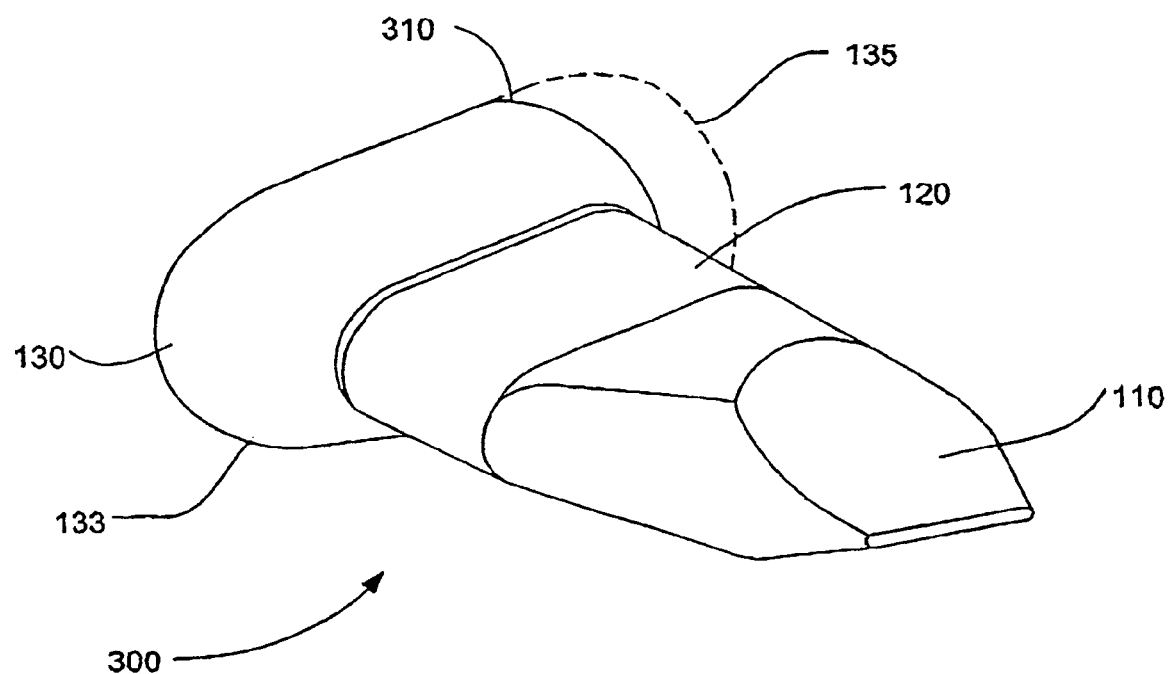
FIGS. 8, 9A, and 9B.
Figure 9A:
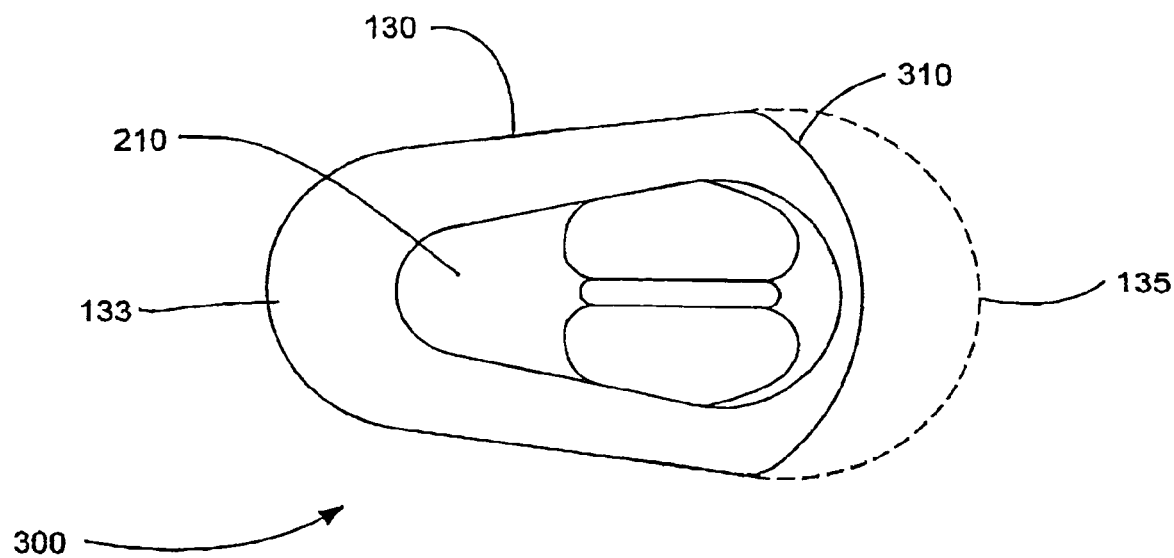
Figure 9B:
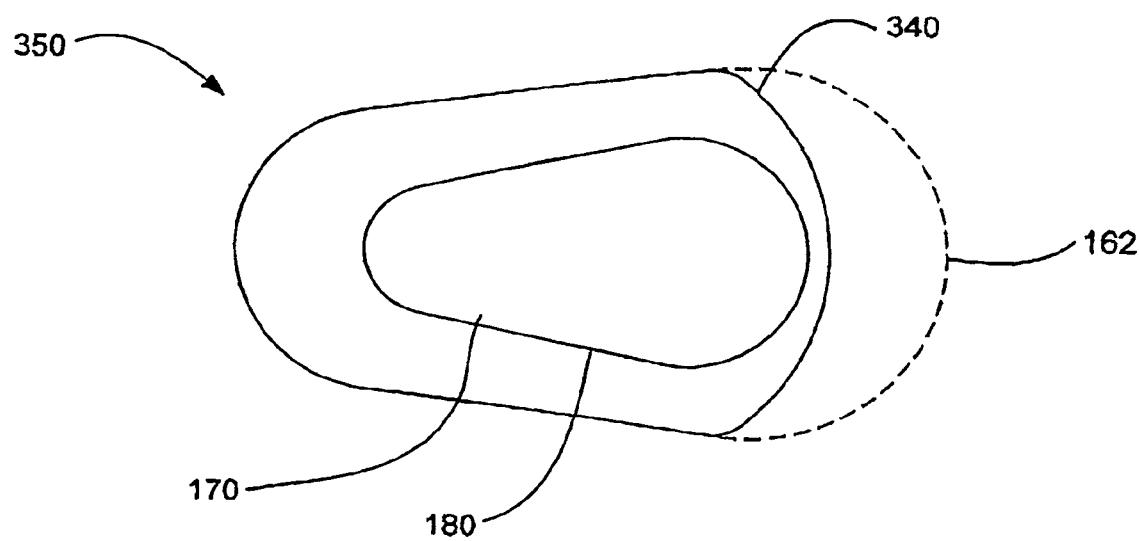

FIGS. 8, 9A, and 9B show a perspective view (FIG. 8) and an end view (FIG. 9A) of another embodiment 300 of the invention, wherein the posterior portion 135 of the teardrop-shaped first wing 130 is truncated at end 310, making the first wing 130 more ovoid. In this configuration, the anterior portion 133 of the first wing 130 is longer than the truncated posterior end 310 of the first wing 130. The embodiment 300 can also have a rotatable spacer 210. It should be appreciated, as illustrated in FIG. 9B, that the second wing in a two-winged version of this embodiment of the invention 300, would be a truncated second wing 350 with a truncated posterior end 340.

The purpose of embodiment 300, as with the other embodiments, is to minimize the possibility of interference of implants positioned between the spinous processes of adjacent pairs of cervical vertebrae, e.g., implants between cervical vertebrae five and six, and between six and seven. During rotation of the neck, the spinous process move past each other in a scissor-like motion. Each cervical vertebra can rotate relative to the next adjacent cervical vertebra in the general range of about 6°-12°. It is to be understood that in addition, about 50 percent of the rotational movement of the neck is accomplished by the top two neck vertebrae. Thus, such embodiments can accommodate neck rotation without adjacent embodiments interfering with each other.

With respect to the prior embodiments which have first and second wings, the second wing 160, FIG. 4 can be designed to be interference-fit onto the spacer 120 or, in the case of a rotatable spacer 210, FIG. 5, a portion of the end of the distraction guide 110 adjacent to the spacer 120. The spacer 120 is associated with the first wing 130. Thus, there is no additional attachment device to fasten the second wing 160 relative to the remainder of the implant. However, as described below and as desired, various fasteners can be used to secure the second wing 160 relative to the remainder of the implant.

Figure 10:
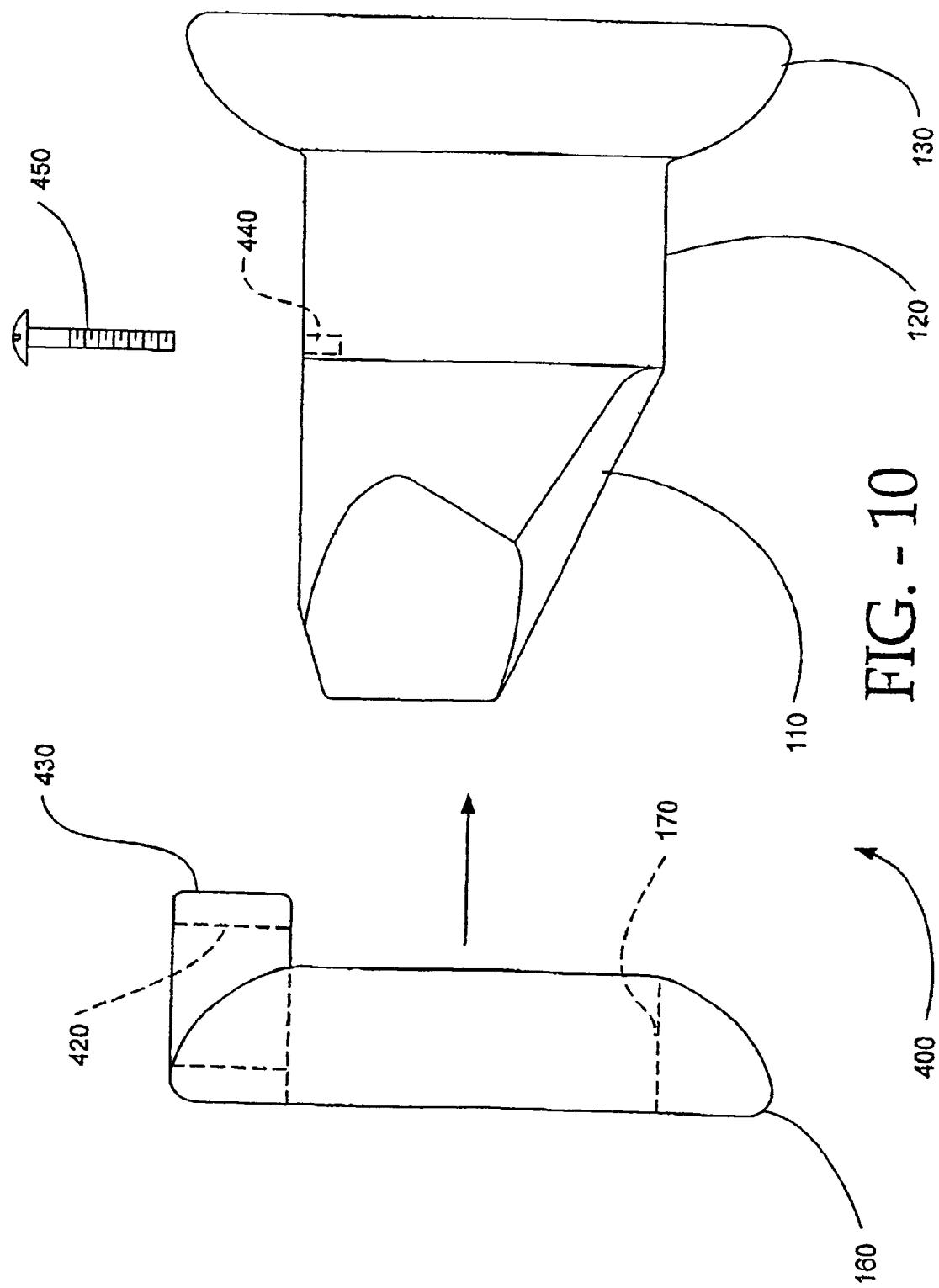
FIGS. 10, 11 and 12.
Figure 11:
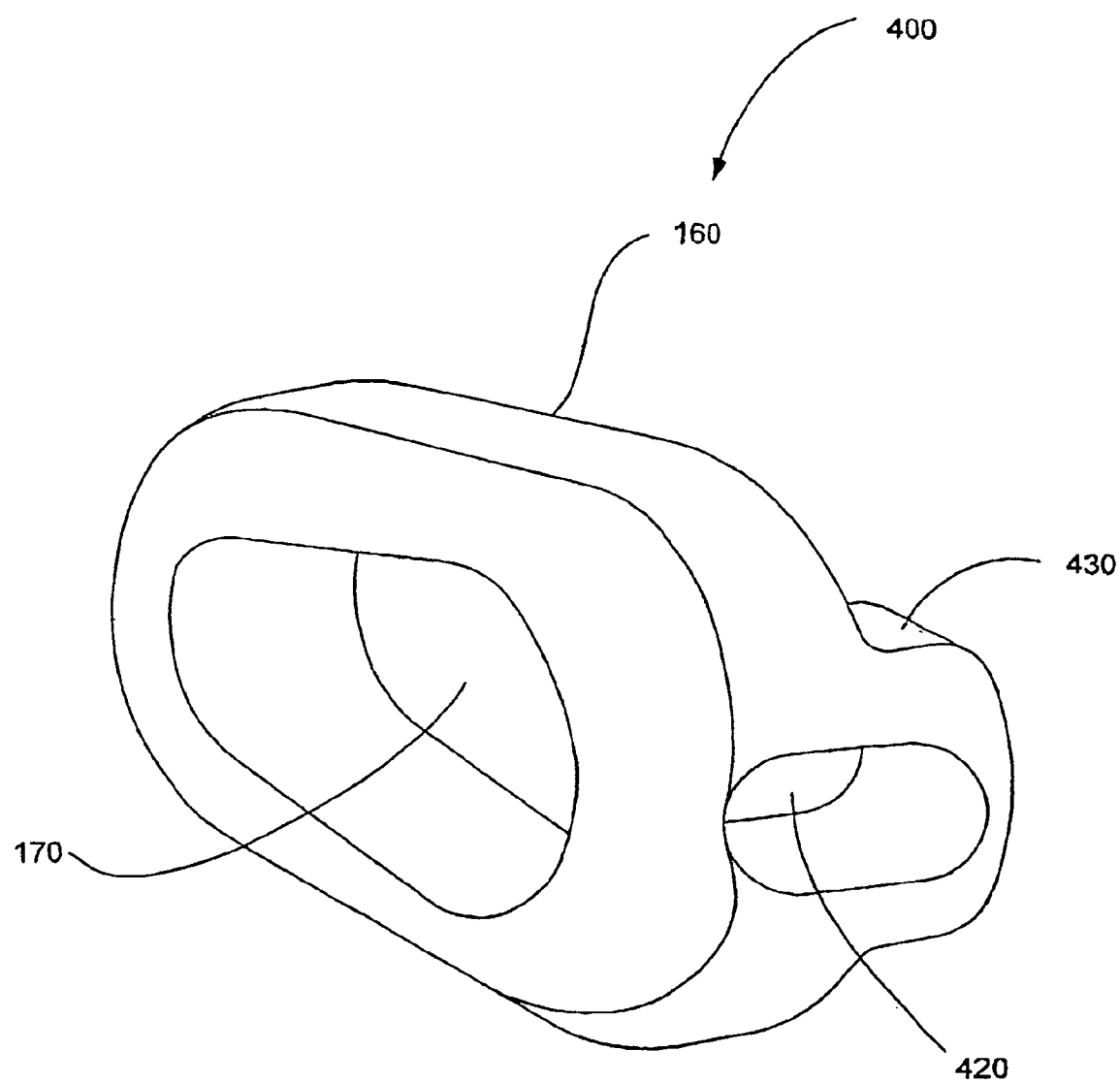
Figure 12:
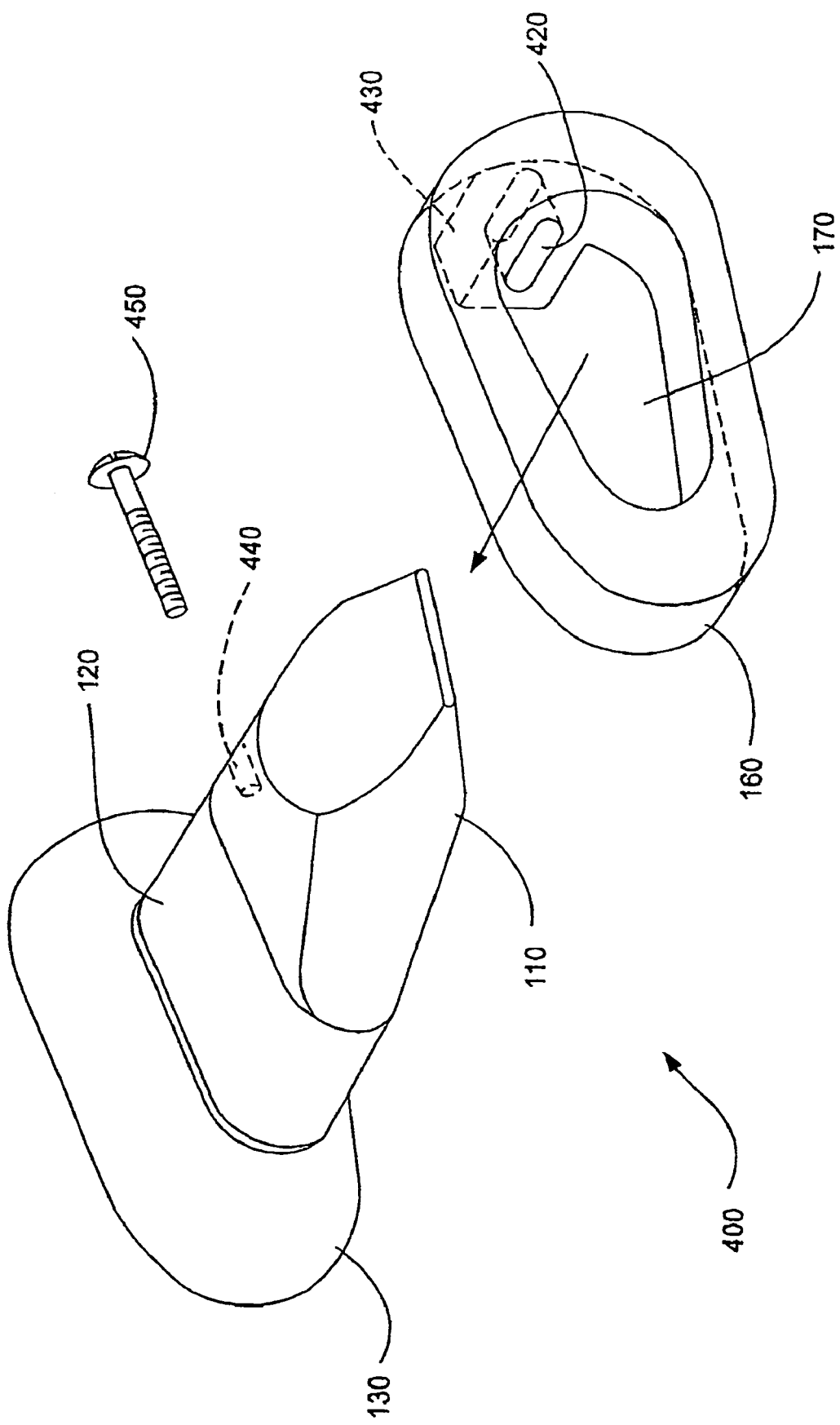
Figure 13A:
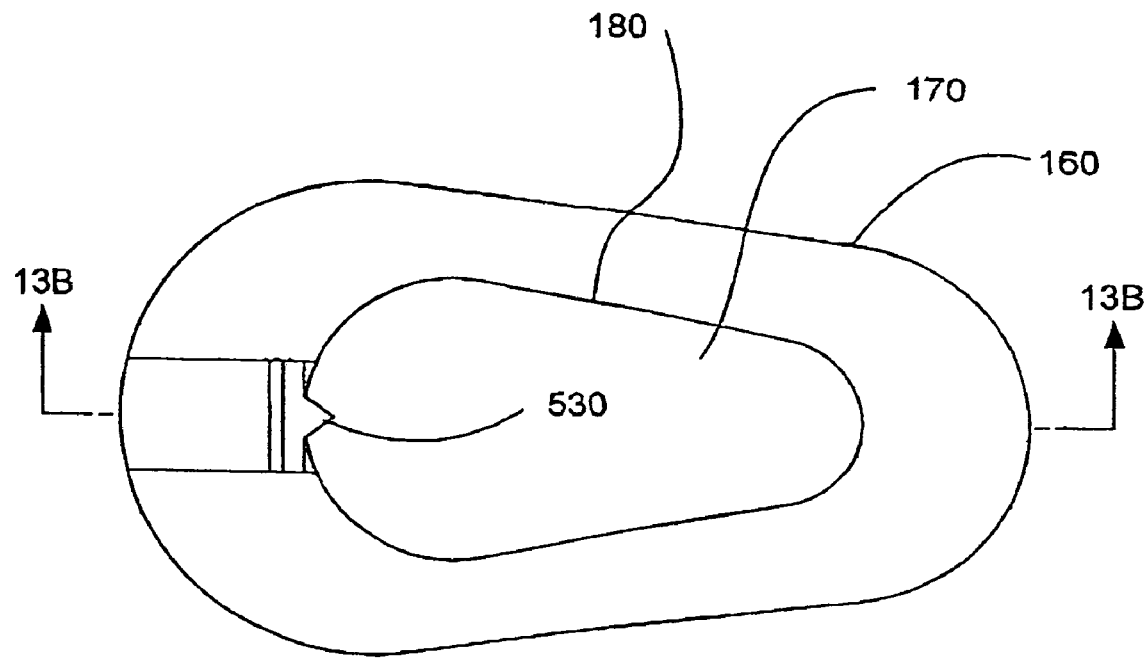
FIGS. 13A, 13B, 14A and 14B.
Figure 13B:
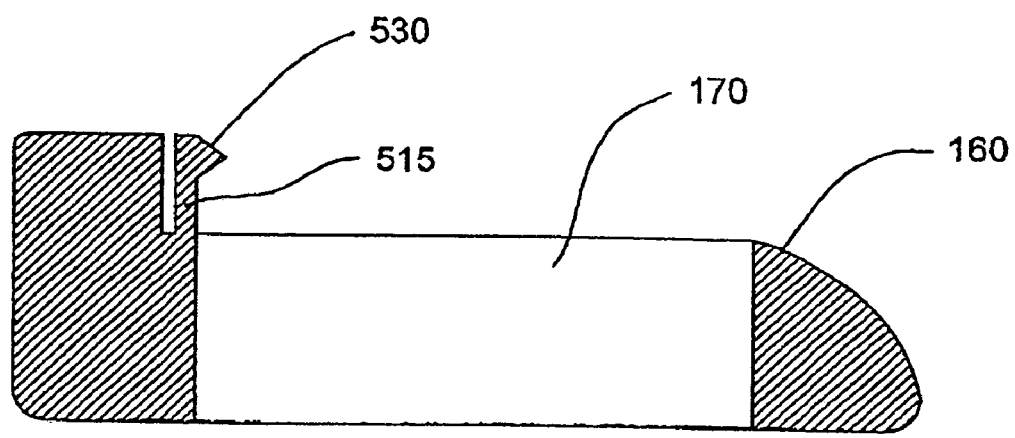
Figure 14A:
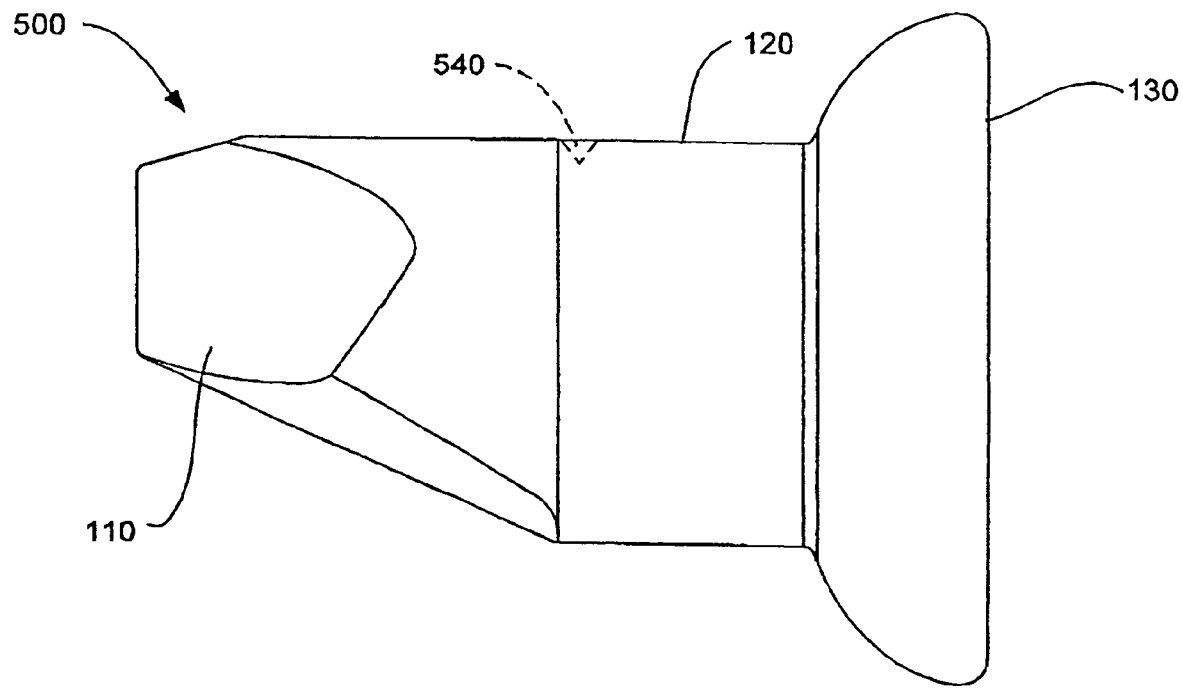
Figure 14B:
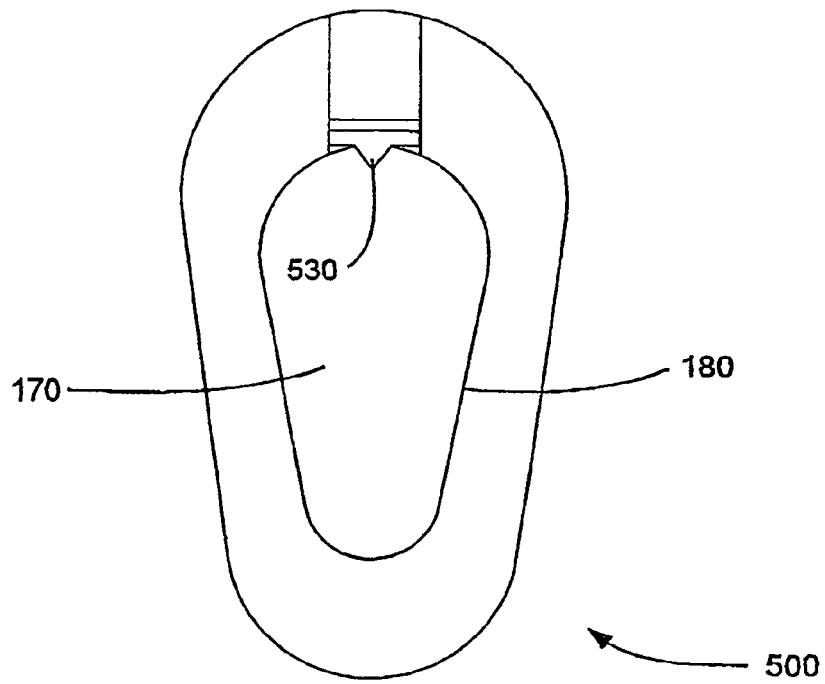

FIGS. 10, 11, and 12 depict an embodiment 400 with a teardrop-shaped second wing 410 that has a bore 420 through a tongue 430 at the posterior end of the second wing 160. The bore on the second wing 420 is brought into alignment with a corresponding bore 440 on the spacer 120 when the second wing 160 is brought into position by surgical insertion relative to the rest of the implant. A threaded screw 450 is inserted through the aligned bores in a posterior-anterior direction to secure the second wing 160 to the spacer 120. The direction of insertion from a posterior to an anterior direction has the screw engaging the bores and the rest of the implant along a direction that is generally perpendicular to the longitudinal axis of the spacer 125 (FIGS. 1 and 3). This orientation is most convenient when the surgeon is required to use screw 450 to secure the second wing 160 to the rest of the implant. Other securing mechanisms using a member inserted into corresponding bores 420, 440 on the spacer 120 and second wing 160 are within the spirit of the invention. It should be understood that a rotatable spacer 210 also can be accommodated by this embodiment. With a rotatable spacer 210, the second wing 160 would be attached to the end of the distraction guide 110 that is located adjacent to 115 the rotatable spacer 210.

FIGS. 13A, 13B, 14A, and 14B depict a further embodiment 500 wherein the second wing 160 is secured to the spacer 120 by a mechanism including a flexible hinge 515, with a protrusion 530 on the end of the hinge 510 adjacent to the lip 180 of the hole 170 defined by portions of the second wing 160. The securing mechanism also encompasses an indentation 540 on the spacer 120, wherein the indentation accommodates the protrusion 530 on the end of the flexible hinge 515. During surgery, after insertion of the distraction guide 110, spacer 120, and first wing 130, the second wing 160 is received over the distraction guide 110 and the spacer 120. As the second wing 160 is received by the spacer 120, the flexible hinge 515 and its protrusion 530 deflect until the protrusion 530 meets adjoins with the indentation 540 in the spacer 120, securing the second wing 160 to the spacer 120. Again in embodiments where the spacer can rotate, the indentation 540 is located on an end of the distraction guide 110 that is adjacent to 150 the rotatable spacer 210. With respect to the flexible hinge 515, this hinge is in a preferred embodiment formed with the second wing 160 and designed in such a way that it can flex as the hinge 515 is urged over the distraction guide 110 and the spacer 120 and then allow the protrusion 530 to be deposited into the indentation 540. Alternatively, it can be appreciated that the indentation 540 can exist in the second wing 160 and the flexible hinge 515 and the protrusion 530 can exist on the spacer 120 in order to mate the second wing 160 to the spacer 120. Still alternatively, the flexible hinge 515 can be replaced with a flexible protrusion that can be flexed into engagement with the indentation 540 in the embodiment with the indentation 540 in the spacer 120 or in the embodiment with the indentation 540 in the second wing 160.

Figure 15A:
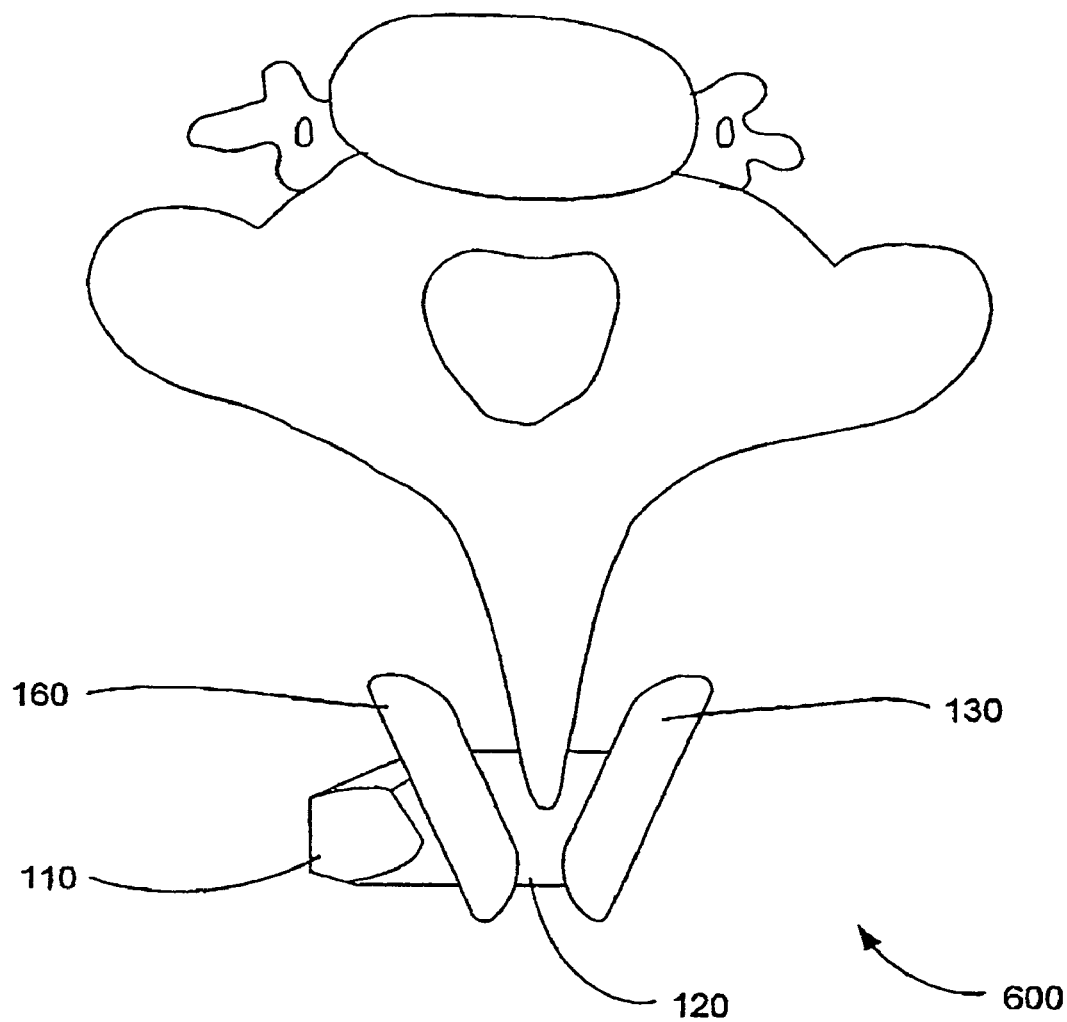
FIGS. 15A, 15B, and 16.
Figure 15B:
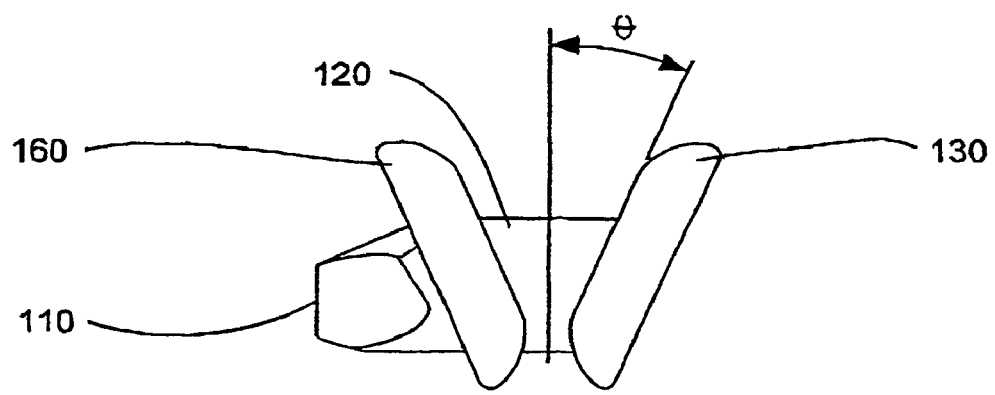
Figure 16:
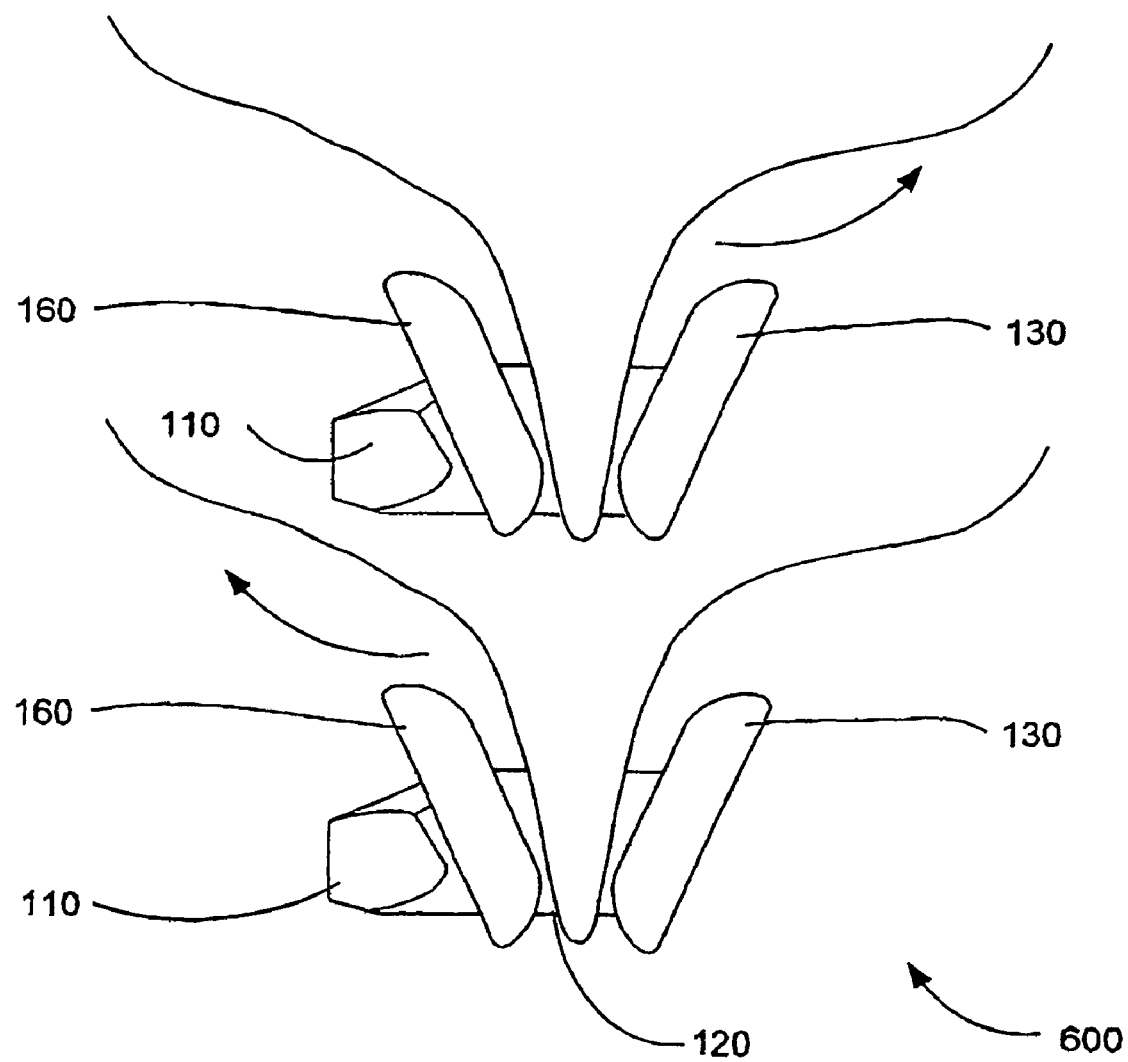

FIGS. 15A, 15B, and 16. These figures illustrate an embodiment 600 wherein the first wing 130 and second wing 160 flare out at an angle away from the spacer 120 and away from each other. That is the anterior ends of the first and second wings flare away from each other. The cervical spinous processes are themselves wedge-shaped when seen from a top view. Accordingly, it is advantageous that the implant 600 accommodate this wedge shape so that the implant 600 can be positioned as close as possible to the vertebral bodies of the spine where the load of the spine is carried. Thus the first 130 and the second wings 160 are positioned relative to the spacer, whether the spacer is fixed 120 or rotatable 210, so that the wings flare out as the wings approach the vertebral body of the spine. FIG. 15B depicts a top view of the implant 600 of FIG. 15A. As is evident from FIG. 15B, the first wing 130 is formed at an angle with respect to a line that is perpendicular to the spacer 120. In a preferred embodiment, the angle is about 30°, with a preferable range θ from about 15° to about 45°. Other angles of the first wing 130 relative to the spacer 120 are contemplated and in accordance with the invention. The second wing 160 is also preferably provided at an angle of about 30° relative to a line that is perpendicular to the spacer with a preferable range θ from about 15° to about 45°. In other words, the wings form an obtuse angle with respect to the spacer 120 in this embodiment. The second wing 160 defines an inner hole 170 which is outlined by the lip 180. As is evident, the lip 180 is provided at an angle relative to the rest of the second wing 160 so that when the lip 180 is urged into contact with the spacer 120, the second wing 160 has the desired angle relative to the spacer 120. As discussed above, there are various ways that the second wing 160 is secured to the spacer 120. FIG. 15A depicts a top view of one such implant 600 placed between the spinous processes of adjacent cervical vertebrae. FIG. 16 is a top view illustrating two layers of distracting implants 600 with flared wings.

Figure 17:
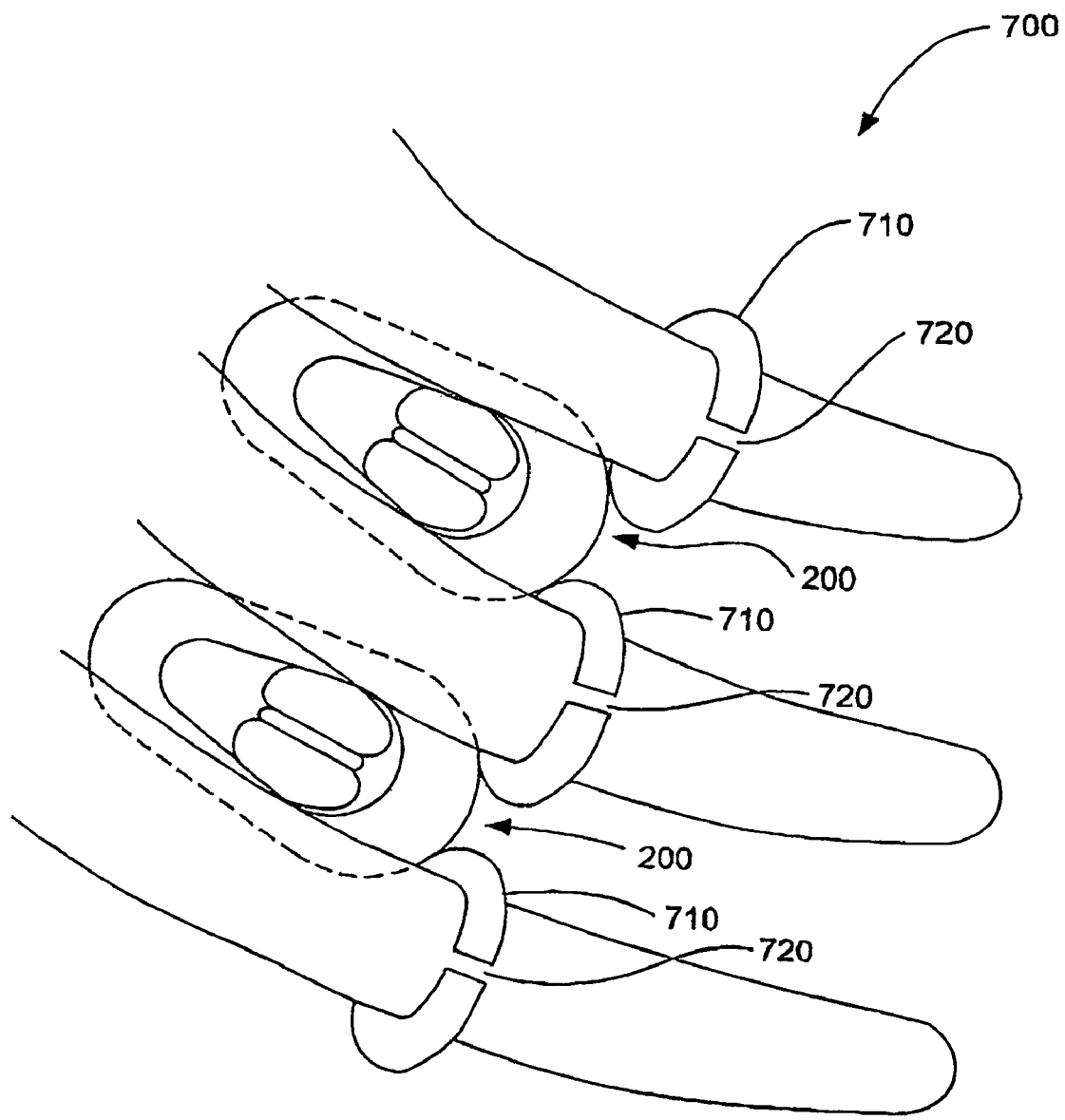
FIG. 17 is a side view of two implants of the invention positioned in the cervical spine, with stops or keeps at the distal ends of the spinous processes.

FIG. 17 illustrates another embodiment 700 that uses "stops" or "keeps" 710, which are rings of flexible biocompatible material, positioned around the spinous processes of adjacent cervical vertebrae and located posteriorly to the implant. The keeps 710 prevent backward displacement of the implants. The keeps generally include a ring 710 which has a slit 720 that goes completely through the ring. The keeps 710 can be somewhat sprung apart, so that the keep 710 can be fit over the end of the spinous process and then allowed to spring back together in order to hold a position on the spinous process. The keep 710 can act as a block to the spacer 120 in order to prevent the implant from movement in a posterior direction.

It is to be understood that the implant and/or portions thereof can be fabricated from somewhat flexible and/or deflectable material. In these embodiments, the implant and/or portions thereof is made out of a polymer, more specifically, the polymer is a thermoplastic. Still more specifically, the polymer is a polyketone known as polyetheretherketone (PEEK). Still more specifically, the material is PEEK450G, which is an unfilled PEEK approved for medical implantation available from Victrex of Lancashire, Great Britain. The Victrex website is located at www.matweb.com, or see Boedeker, at www.boedeker.com. Other sources of this material include Gharda located in Panoli, India, at www.ghardapolymers.com. The implant and/or portions thereof can be formed by extrusion, injection, compression molding and/or machining techniques. The material specified has appropriate physical and mechanical properties and is suitable for carrying and spreading the physical load between the spinous process. Further in-this embodiment, the PEEK has the following additional approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

In an another preferred embodiment, the implant is comprised at least, in part of titanium or stainless steel, or other suitable implant material which may be radiopaque and, in part, of a radiolucent material that does not show up under x-ray or other type of imaging. In a preferred embodiment, the first wing 130 and second wing 160 and the shaft 230 are comprised of such a radiopaque material such as titanium and the spacer 120 and the distraction guide 110 are comprised of a radiolucent material such as, for example, PEEK or other radiolucent materials described herein. In an embodiment which includes the first wing 130, with the spacer 120 and the distraction guide 110, under imaging, the implant looks like a "T". In an embodiment which includes both a first and a second wing, the spacer and the tissue expander, under imaging, the implant looks like an "H". This embodiment allows the doctor to have a clearer view of the spine under imaging without the implant interfering as much with the view of the bone structure. Alternatively, the entire implant can be comprised of titanium or stainless steel.

It should be noted that the material selected may also be filled. For example, other grades of PEEK are also available and contemplated, such as 30% glass-filled or 30% carbon-filled, provided such materials are cleared for use in implantable devices bythe FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the implant is manufactured from PEEK, available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK).

Other material that can be used include polyetherketone (PEK), polyetherketoneetherketoneketone (PEKEKK), and polyetheretherketoneketone (PEEKK), and generally a polyaryletheretherketone. Further, other polyketones can be used as well as other thermoplastics.

Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 18:
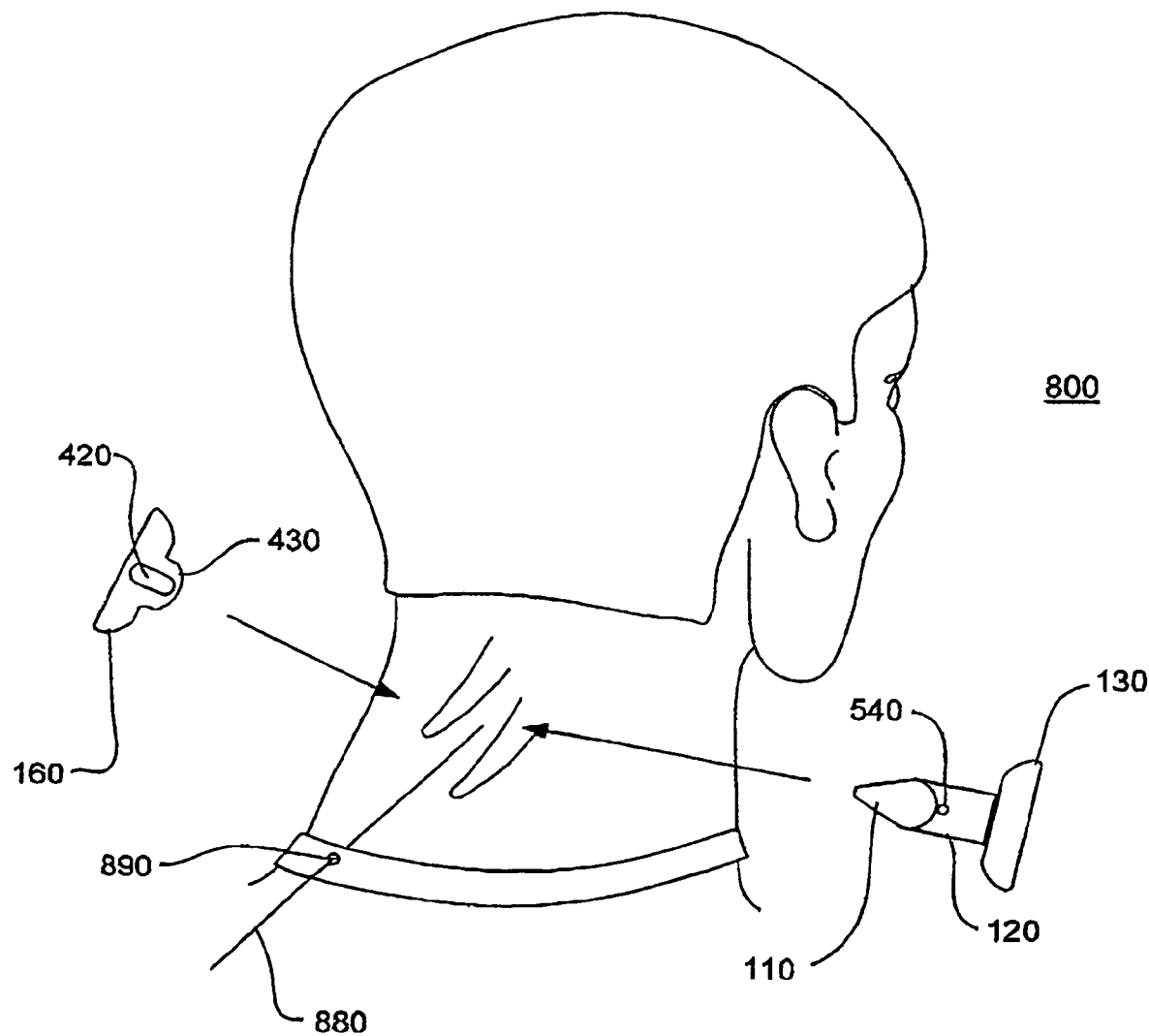
FIG. 18 depicts a method of the invention for surgically implanting an embodiment of the implant of the invention adjacent to cervical spinous processes of a patient.

A minimally invasive surgical method for implanting the cervical distraction device in the cervical spine is disclosed and taught herein. In this method, FIG. 18, preferably a guide wire 880 is inserted through a placement network 890 into the neck of the implant recipient. The guide wire 880 is used to locate where the implant is to be placed relative to the cervical spine, including the spinous processes. Once the guide wire 880 is positioned with the aid of imaging techniques, an incision is made on the side of the neck about so that the first unit of the embodiment of the invention, which includes the distraction guide 110, the spacer 120, and the first wing 130 can be positioned in the neck thorough an incision and along a line that is about perpendicular to the guide wire 880 and directed at the end of the guide wire. The first unit is so inserted into the neck of the patient. Preferably during insertion, the distraction end pokes through or separates the tissue without severing the tissue. Next, the second wing 160 is inserted along a line that is generally colinear with the line over which the first unit is inserted but from the opposite side of the neck. The anatomy of the neck is such that it is most convenient and minimally invasive to enter the neck from the side with respect to the first unit and the second wing 160. The second wing 160 is mated to the first unit and, in this particular embodiment, the second wing 160 is snapped into engagement with the first unit. In an alternative embodiment, the second wing 160 is attached to-the first unit by the use of a fastener, and in particular by a screw 450. The screw 450 is positioned using a screw driving mechanism that is directed along a posterior to anterior line somewhat parallel to the guide wire 880. This posterior to anterior line aids the physician in viewing and securing the second wing 160 to the first unit.

It is to be understood that the various features of the various embodiments can be combined with other embodiments of the invention and be within the spirit and scope of the invention. Thus, for example only, the embodiment of FIG. 1 can have truncated wings as depicted in other embodiments.

INDUSTRIAL APPLICABILITY

The above establishes that the present invention can be used to relieve pain associated with the cervical spine. The present invention is minimally invasive and can be used on an outpatient basis.

Additional aspects, objects and advantages of the invention can be obtained through a review of the appended claims and figures.

It is to be understood that other embodiments can be fabricated and come within the spirit and scope of the claims.

The foregoing description of preferred embodiments of the present invention has been provided for the purposes of illustration and description. It is not intended to be exhaustive or to limit the invention to the precise forms disclosed. Many modifications and variations will be apparent to one of the ordinary skill in the relevant arts. The embodiments were chosen and described in order to best explain the principles of the invention and its partial application, thereby enabling others skilled in the art to understand the invention for various embodiments and with various modifications that are suited to the particular use contemplated. It is intended that the scopes of the invention are defined by the claims and their equivalence.

What is claimed:

1. A spinal implant comprising:
   a spacer having a longitudinal axis and first and second end portions; said spacer further having an anterior edge and a posterior edge and elongated therebetween in a first direction generally transverse to said longitudinal axis;
   a first wing disposed proximate said first end portion and disposed generally transverse to said longitudinal axis; said first wing elongated from a posterior edge to an anterior edge thereof in said first direction;
   a distraction guide disposed more proximate said second end portion than said first end portion and tapering away from said first wing;
   a second wing disposed proximate said second end portion and said distraction guide, said second wing disposed generally transverse to said longitudinal axis and removably mounted to at least one of said spacer and said distraction guide; said second wing elongated from a posterior edge to an anterior edge thereof in said first direction;
   wherein the anterior and posterior edges of said spacer are generally rounded, said spacer further having generally linear surfaces disposed between said anterior and posterior edges disposed so as to diverge from each other toward said posterior edge so that said spacer creates a wedge narrowing in said first direction;
   wherein the spacer is rotatable about said longitudinal axis so as to be variably positioned rotationally relative to said first wing while said spacer is coupled to said first wing.

2. The implant of claim 1 wherein said second wing comprises a hole therethrough disposed along said longitudinal axis and sized to allow said second wing to be received over said distraction guide with a tip of said distraction guide passing through said hole.

3. The implant of claim 1 wherein, in cross-sectional view of said spacer normal to said longitudinal axis, a largest height of said posterior edge of said spacer taken perpendicular to a theoretical line extending between said anterior and posterior edges is greater than a corresponding largest height of said anterior edge of said spacer.

4. The implant of claim 1 wherein the spacer can rotate relative to the wing and the distraction guide.

5. The implant of claim 1 wherein said spacer, when urged between the spinous process of the adjacent cervical vertebrae, allows flexion but not extension and creates a contact surface with the bone of the spinous processes that increases as the wedge-like spacer moves anteriorly.

6. The implant in claim 1 wherein the first wing and the second wing are angled outward relative to each other to accommodate the anatomy of the adjacent spinous processes of the cervical spine.

7. The implant of claim 1 wherein the second wing has a rounded anterior edge and a rounded posterior edge and is elongated therebetween in said first direction; said second wing further having generally linear surfaces disposed between said second wing anterior and posterior edges disposed so as to diverge from each other toward said second wing posterior edge.

8. The implant of claim 7 wherein the anterior and posterior edges of said first wing are generally rounded, said first wing further having generally linear surfaces disposed between said first wing anterior and posterior edges disposed so as to diverge from each other toward said first wing posterior edge.

9. The implant of claim 3 wherein the second wing has an anterior edge and a posterior edge corresponding to said anterior and posterior edges of said spacer, respectively; wherein, in cross-sectional view of said second wing generally normal to said longitudinal axis, a largest height of said posterior edge of said second wing taken perpendicular to a theoretical line extending between said second wing anterior and posterior edges is greater than a corresponding largest height of said anterior edge of said second wing.

10. The implant of claim 9 wherein, in cross-sectional view of said first wing generally normal to said longitudinal axis, a largest height of said posterior edge of said first wing taken perpendicular to a theoretical line extending between said first wing anterior and posterior edges is greater than a corresponding largest height of said anterior edge of said first wing.

11. A method for implanting an implant between spinous processes comprising the steps of:
    inserting a first portion of the implant including a spacer and a distraction end laterally between adjacent spinous processes; said spacer having:
      a longitudinal axis and first and second end portions;
      an anterior edge and a posterior edge and elongated therebetween in a first direction generally transverse to said longitudinal axis;
    said first portion comprising a first wing disposed proximate said spacer first end portion and disposed generally transverse to said longitudinal axis;
    inserting a second portion of the implant including a second wing laterally from an opposite direction from the insertion of the first portion such that said second wing is disposed proximate said second end portion and said distraction end and generally transverse to said longitudinal axis; and
    fastening the second portion to the first portion;
    wherein, after said fastening, said first wing, said second wing, and said spacer are elongated in a posterior to anterior direction with respect to the adjacent spinous processes.

12. The method of claim 11 wherein the fastening step includes interference-fitting the second portion onto the first portion.

13. The method of claim 11 including implanting the implant without severing the ligamentum nuchae.

14. The method of claim 11 including implanting the implant without altering the spinous processes.

15. The method of claim 11 including implanting the implant without severing the supraspinous ligament.

16. The method of claim 11 wherein said inserting said first position of the implant between adjacent spinous processes comprises inserting said first portion of the implant between adjacent spinous processes of cervical vertebrae.

17. The method of claim 11 wherein said inserting said second portion of the implant comprises inserting said distraction end into a hole in said second wing.

18. The method of claim 11 wherein said anterior and posterior edges of said spacer are generally rounded, said spacer further having generally planar surfaces disposed between said anterior and posterior edges disposed so as to diverge from each other toward said posterior edge; wherein, after said fastening, said planar surfaces contact respective adjacent spinous processes.

19. The method of claim 11 wherein said inserting a first portion of the implant comprises rotating said spacer about a longitudinal axis thereof.

20. The method of claim 11 wherein said inserting a first portion of the implant comprises orienting a narrower cross-sectional portion of said spacer anteriorly and an thicker cross-sectional portion of said spacer posteriorly by rotating said spacer relative to said first wing.

* * * * *